(12) United States Patent
Ries et al.

(10) Patent No.: US 7,425,641 B2
(45) Date of Patent: Sep. 16, 2008

(54) CARBOXYLIC ACID AMIDES, THE PREPARATION THEREOF AND THEIR USE AS PHARMACEUTICAL COMPOSITIONS

(75) Inventors: Uwe Ries, Biberach (DE); Henning Priepke, Warthausen (DE); Armin Heckel, Biberach (DE); Herbert Nar, Ochsenhausen (DE); Wolfgang Wienen, Biberach (DE); Jean Marie Stassen, Lubbeek (BE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 10/938,804

(22) Filed: Sep. 10, 2004

(65) Prior Publication Data
US 2005/0065346 A1 Mar. 24, 2005

Related U.S. Application Data

(63) Continuation of application No. 10/049,196, filed on Oct. 9, 2002, now abandoned.

(30) Foreign Application Priority Data

| Aug. 7, 1999 | (DE) | 199 37 494 |
| May 24, 2000 | (DE) | 100 25 663 |
| Aug. 2, 2000 | (WO) | PCT/EP00/07457 |

(51) Int. Cl.
C07D 272/02 (2006.01)
C07D 211/06 (2006.01)
A61K 31/40 (2006.01)
A61K 31/445 (2006.01)

(52) U.S. Cl. ......... 548/530; 546/226; 514/423; 514/330

(58) Field of Classification Search ......... 546/226; 548/530; 514/423, 330
See application file for complete search history.

(56) References Cited

U.S. PATENT DOCUMENTS

| 5,726,159 A | 3/1998 | Schacht |
| 2002/0151595 A1 | 10/2002 | Ries et al. |

FOREIGN PATENT DOCUMENTS

| CA | 2 380 986 A1 | 2/2001 |
| CA | 2 436 837 A1 | 8/2002 |
| DE | 199 37 494 A1 | 2/1999 |
| EP | 0 306 827 A1 | 9/1988 |
| EP | 1 206 446 B1 | 5/2002 |
| GB | 2 007 663 A1 | 5/1979 |
| JP | 1-93568 A | 4/1989 |
| JP | 04-249551 A | 4/1992 |
| WO | 98/46576 A2 | 10/1998 |
| WO | 02/062748 A1 | 8/2002 |
| WO | WO02/062748 A1 * | 8/2002 |
| WO | 03/035602 A1 | 5/2003 |

OTHER PUBLICATIONS

Wolff, Manfred E. "Burger's Medicinal Chemistry, 5ed, Part I", John Wiley & Sons, 1995, pp. 975-977.*
Banker (Modern Pharmaceutics) Banker, G.S. et al, "Modern Pharmaceutics, 3ed.", Marcel Dekker, New York, 1996, pp. 451 and 596.*
Sakaguchi, Jun et al; "Synthesis Gastrointestinal Prokinetic Activity and Structure-Activity Relationships of Novel N-[[2-(Dialkylamino)ethoxy]benzyl]benzamide Derivatives"; 1992; Chem. Pharma. Bull. 40(I) 202-211; XP-002152593.
Simon, L. et al; "Darstellung von substituierten Isochinolinderivaten"; 1974; Pharmazie 29, H. 5 XP-002152594.
Labes, D. et al; "Free-Wilson-Analyseder Hemmwirkung von 4-substituierten Benzamidinen gegenueber Thrombin, Plasim und Trypsin"; 1979; Pharamzie 34, H.9 XP002152595.
Niels Mork Nielsen et al; Prodrugs as Drug Delivery Systems. 68. Chemical and Plasma-Catalyzed Hydrolysis of Various Esters of Benzoic Acid: A Reference System for Designing Prodrug Esters of Carboxylic Acid Agents; International Journal of Pharmaceutics (1987) vol. 39 pp. 75-85.
International Search Report for PCT/EP00/07457 mailed on Dec. 1, 2000.

* cited by examiner

*Primary Examiner*—Rita J Desai
(74) *Attorney, Agent, or Firm*—Michael P. Morris; Edouard G. Lebel; David A. Dow

(57) ABSTRACT

The present invention relates to carboxylic acid amides of general formula

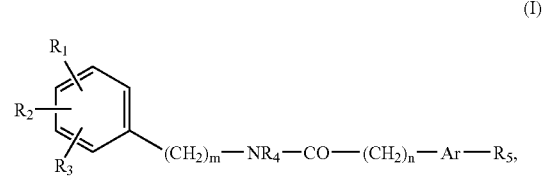

(I)

wherein
$R_1$ to $R_5$, Ar, m and n are defined as in claim 1, the tautomers, stereoisomers, mixtures thereof, the prodrugs and the salts thereof which have valuable properties.

The compounds of the above general formula I wherein $R_5$ denotes a cyano group are valuable intermediate products for preparing the other compounds of general formula I, and the compounds of the above general formula I wherein $R_5$ denotes one of the amidino groups mentioned in claim 1 have valuable pharmacological properties, particularly an antithrombotic activity and a factor Xa-inhibiting activity.

9 Claims, No Drawings

CARBOXYLIC ACID AMIDES, THE PREPARATION THEREOF AND THEIR USE AS PHARMACEUTICAL COMPOSITIONS

This application is a continuation of U.S. application Ser. No. 10/049,196 filed Oct. 9, 2002, now abandoned, the contents of which are incorporated herein. This application also claims the benefit of PCT EP00/07457, filed Aug. 2, 2000, DE 19937494 filed Aug. 7, 1999 and DE 10025663 filed May 24, 2000 the contents or which are also incorporated herein.

The present invention relates to carboxylic acid amides of general formula

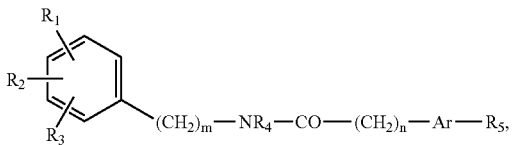

(I)

their tautomers, stereoisomers, mixtures thereof, the prodrugs thereof, the derivatives thereof which contain a group which is negatively charged under physiological conditions, and the salts thereof, particularly the physiologically acceptable salts thereof with inorganic or organic acids or bases which have valuable properties.

The compounds of the above general formula I wherein $R_5$ denotes a cyano group, are valuable intermediate products for preparing the above compounds of general formula I, and the compounds of the above general formula I wherein $R_5$ denotes one of the following amidino groups, as well as their tautomers, stereoisomers, mixtures thereof, the prodrugs thereof, the derivatives thereof which contain a group which is negatively charged under physiological conditions, and the salts thereof, particularly the physiologically acceptable salts thereof with inorganic or organic acids, and the stereoisomers thereof have valuable pharmacological properties, particularly an antithrombotic activity and a factor Xa-inhibiting activity.

The present application thus relates to the new compounds of the above general formula I and their preparation, pharmaceutical compositions containing the pharmacologically active compounds, the preparation and use thereof.

In the above general formula
one of the groups m or n denotes the number 0 and
the other group m or n denotes the number 1,
Ar denotes a phenylene or naphthylene group optionally substituted by a fluorine, chlorine or bromine atom, by a trifluoromethyl, $C_{1-3}$-alkyl, hydroxy, $C_{1-3}$-alkoxy, phenyl-$C_{1-3}$-alkoxy, amino, $C_{1-3}$-alkylamino or di-($C_{1-3}$-alkyl)-amino group, whilst the phenylene group may be substituted by another fluorine, chlorine or bromine atom or by another $C_{1-3}$-alkyl group,
a thienylene, thiazolylene, pyridinylene, pyrimidinylene, pyrazinylene or pyridazinylene group optionally substituted in the carbon skeleton by a $C_{1-3}$-alkyl group,
$R_1$ denotes a $C_{1-3}$-alkyl group optionally substituted by an amino, $C_{1-3}$-alkylamino, di-($C_{1-3}$-alkyl)-amino, phenyl, naphthyl, heteroaryl or 4- to 7-membered cycloalkyleneimino group,
a $C_{3-7}$-cycloalkyl group which is substituted in the 1 position by a 5- to 7-membered cycloalkyleneiminocarbonyl group,
an amino, $C_{1-5}$-alkylamino, $C_{5-7}$-cycloalkylamino or phenyl-$C_{1-3}$-alkylamino group which 20 may in each case be substituted at the amino-nitrogen atom by a benzoyl or phenylsulphonyl group or by a $C_{1-3}$-alkyl or $C_{1-3}$-alkylcarbonyl group optionally substituted in the $C_{1-3}$-alkyl moiety by a carboxy group,
a 4- to 7-membered cycloalkyleneiminocarbonyl or cycloalkyleneiminosulphonyl group optionally substituted by a $C_{1-3}$-alkyl group,
an aminosulphonyl group optionally substituted by one or two $C_{1-3}$-alkyl groups,
a phenyl group optionally substituted by a fluorine, chlorine or bromine atom, by a trifluoromethyl, aminosulphonyl, $C_{1-3}$-alkyl or $C_{1-3}$-alkoxy group, which may additionally be substituted by a fluorine, chlorine or bromine atom or by a trifluoromethyl, $C_{1-3}$-alkyl or $C_{1-3}$-alkoxy group,
a $C_{1-3}$-alkoxy, phenyl-$C_{1-3}$-alkoxy, heteroaryloxy or heteroaryloxy-$C_{1-3}$-alkoxy group wherein the alkoxy moiety may be substituted in the 2 or 3 position in each case by an amino, $C_{1-3}$-alkylamino or di-($C_{1-3}$-alkyl)-amino group,
a $C_{3-7}$-cycloalkoxy group, whilst the methylene group in the 3 or 4 position in a $C_{5-7}$-cycloalkoxy group may be replaced by an —NH group, whilst the —NH group may be substituted
by a $C_{1-3}$-alkyl group which may be substituted in the 2 or 3 position by an amino, $C_{1-3}$-alkylamino or di-($C_{1-3}$-alkyl)-amino group, by a $C_{1-3}$-alkylcarbonyl, arylcarbonyl or arylsulphonyl group or
by an aminocarbonyl, $C_{1-3}$-alkylaminocarbonyl or di-($C_{1-3}$-alkyl)-aminocarbonyl group, wherein in each case the oxygen atom of the carbonyl group is replaced by an imino group,
$R_2$ denotes a hydrogen, fluorine, chlorine or bromine atom, a $C_{1-3}$-alkyl, hydroxy or $C_{1-3}$-alkoxy group,
$R_3$ denotes a hydrogen atom or a $C_{1-3}$-alkyl group,
$R_4$ denotes a hydrogen atom or a $C_{1-3}$-alkyl group optionally substituted by a carboxy group and
$R_5$ denotes a cyano group or an amidino group optionally substituted by one or two $C_{1-3}$-alkyl groups,
but particularly, if m, n, Ar and $R_2$ to $R_5$ are as hereinbefore defined,
$R_1$ denotes a $C_{1-3}$-alkyl group optionally substituted by an amino, $C_{1-3}$-alkylamino, di-($C_{1-3}$-alkyl)-amino, phenyl, naphthyl or heteroaryl group,
a $C_{3-7}$-cycloalkyl group which is substituted in the 1 position by a 5- to 7-membered cycloalkyleneiminocarbonyl group,
a 4- to 7-membered cycloalkyleneiminocarbonyl group,
a phenyl group optionally substituted by a fluorine, chlorine or bromine atom, by a trifluoromethyl, $C_{1-3}$-alkyl or $C_{1-3}$-alkoxy group,
a $C_{1-3}$-alkoxy, phenyl-$C_{1-3}$-alkoxy, heteroaryloxy or heteroaryloxy-$C_{1-3}$-alkoxy group wherein the alkoxy moiety in the 2 or 3 position may be substituted in each case by an amino, $C_{1-3}$-alkylamino or di-($C_{1-3}$-alkyl)-amino group,
a $C_{3-7}$-cycloalkoxy group, whilst the methylene group in the 3 or 4 position in a $C_{5-7}$-cycloalkoxy group may be replaced by an —NH group, whilst the —NH group may be substituted by an arylcarbonyl or arylsulphonyl group, by a $C_{1-3}$-alkylcarbonyl group wherein the oxygen atom of the carbonyl group may be replaced by an imino group and the alkanoyl moiety may be substituted by an amino, $C_{1-3}$-alkylamino or di-($C_{1-3}$-alkyl)-amino group, or by a $C_{1-3}$-alkyl group which may be substituted in the 2 or 3 position by an amino, $C_{1-3}$-alkylamino or di-($C_{1-3}$-alkyl)-amino group,
in particular
$R_1$ denotes a $C_{1-3}$-alkyl group substituted by a 4- to 7-membered cycloalkyleneimino group, an amino, $C_{1-5}$-alkylamino, $C_{5-7}$-cycloalkylamino or phenyl-$C_{1-3}$-alkylamino group which may in each case be substituted at the amino-nitrogen atom by a benzoyl or phenylsulphonyl group or by a $C_{1-3}$-alkyl or $C_{1-3}$-alkylcarbonyl group optionally substituted in the $C_{1-3}$-alkyl moiety by a carboxy group, a 4- to 7-membered cycloalkyleneiminocarbonyl group substituted by a $C_{1-3}$-alkyl group, a 4- to 7-membered cycloalkyleneiminosulphonyl group optionally substituted by a $C_{1-3}$-alkyl group, an aminosulphonyl group optionally substituted by one or two $C_{1-3}$-alkyl groups, an aminosulphonylphenyl group, a phenyl group substituted by a fluorine, chlorine or bromine atom, by a trifluoromethyl, aminosulphonyl, $C_{1-3}$-alkyl or $C_{1-3}$-alkoxy group, which may additionally be substituted by a fluorine, chlorine or bromine atom or by a trifluoromethyl, $C_{1-3}$-alkyl or $C_{1-3}$-alkoxy group, a $C_{3-7}$-cycloalkoxy group, whilst the methylene group in the 3 or 4 position is replaced in a $C_{5-7}$-cycloalkoxy group by an —NH group, whilst the —NH group is substituted by an aminocarbonyl, $C_{1-3}$-alkylaminocarbonyl or di-($C_{1-3}$-alkyl)-aminocarbonyl group, wherein in each case the oxygen atom of the carbonyl group is replaced by an imino group.

By the abovementioned heteroaryl groups is meant a 5-membered heteroaryl group optionally substituted by a $C_{1-3}$-alkyl group which contains, in the heteroaromatic moiety, an imino group optionally substituted by a $C_{1-3}$-alkyl group, or an oxygen or sulphur atom, an imino group optionally substituted by a $C_{1-3}$-alkyl group and an oxygen, sulphur or nitrogen atom, an imino group optionally substituted by a $C_{1-3}$-alkyl group and two nitrogen atoms or an oxygen or sulphur atom and two nitrogen atoms, or a 6-membered heteroarylene group optionally substituted by a $C_{1-3}$-alkyl group which contains one or two nitrogen atoms in the heteroaromatic moiety.

Moreover, the carboxy groups mentioned in the definition of the abovementioned groups may be replaced by a group which may be converted into a carboxy group in vivo or by a group which is negatively charged under physiological conditions or the amino and imino groups mentioned in the definition of the abovementioned groups may be replaced by a group which may be cleaved in vivo. Groups of this kind are described for example in WO 98/46576 and by N. M. Nielsen et al. in International Journal of Pharmaceutics 39, 75-85 (1987).

By a group which can be converted in vivo into a carboxy group is meant, for example, a hydroxymethyl group, a carboxy group esterified with an alcohol, wherein the alcoholic moiety preferably denotes a $C_{1-6}$-alkanol, a phenyl-$C_{1-3}$-alkanol, a $C_{3-9}$-cycloalkanol, whilst a $C_{5-8}$-cycloalkanol may additionally be substituted by one or two $C_{1-3}$-alkyl groups, a $C_{5-8}$-cycloalkanol wherein a methylene group in the 3 or 4 position is replaced by an oxygen atom or by an imino group optionally substituted by a $C_{1-3}$-alkyl, phenyl-$C_{1-3}$-alkyl, phenyl-$C_{1-3}$-alkoxycarbonyl or $C_{2-6}$-alkanoyl group and the cycloalkanol moiety may additionally be substituted by one or two $C_{1-3}$-alkyl groups, a $C_{4-7}$-cycloalkenol, a $C_{3-5}$-alkenol, a phenyl-$C_{3-5}$-alkenol, a $C_{3-5}$-alkynol or phenyl-$C_{3-5}$-alkynol, with the proviso that no bond to the oxygen atom starts from a carbon atom which carries a double or triple bond, a $C_{3-8}$-cycloalkyl-$C_{1-3}$-alkanol, a bicycloalkanol having a total of 8 to 10 carbon atoms which may additionally be substituted by one or two $C_{1-3}$-alkyl groups in the bicycloalkyl moiety, a 1,3-dihydro-3-oxo-1-isobenzfuranol or an alcohol of formula

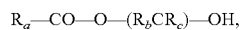

$$R_a\text{—CO—O—}(R_bCR_c)\text{—OH},$$

wherein $R_a$ denotes a $C_{1-8}$-alkyl, $C_{5-7}$-cycloalkyl, phenyl or phenyl-$C_{1-3}$-alkyl group, $R_b$ denotes a hydrogen atom, a $C_{1-3}$-alkyl, $C_{5-7}$-cycloalkyl or phenyl group and $R_c$ denotes a hydrogen atom or a $C_{1-3}$-alkyl group, by a group which is negatively charged under physiological conditions is meant a tetrazol-5-yl, phenylcarbonylaminocarbonyl, trifluoromethylcarbonylaminocarbonyl, $C_{1-6}$-alkylsulphonylamino, phenylsulphonylamino, benzylsulphonylamino, trifluoromethylsulphonylamino, $C_{1-6}$-alkylsulphonylaminocarbonyl, phenylsulphonylaminocarbonyl, benzylsulphonylaminocarbonyl or perfluoro-$C_{1-6}$-alkylsulphonylaminocarbonyl group and by a group which can be cleaved in vivo from an imino or amino group is meant, for example, a hydroxy group, an acyl group such as a benzoyl group optionally mono- or disubstituted by fluorine, chlorine, bromine or iodine atoms or by $C_{1-3}$-alkyl or $C_{1-3}$-alkoxy groups, whilst the substituents may be identical or different, a pyridinoyl group or a $C_{1-16}$-alkanoyl group such as the formyl, acetyl, propionyl, butanoyl, pentanoyl or hexanoyl group, a 3,3,3-trichloropropionyl or allyloxycarbonyl group, a $C_{1-16}$-alkoxycarbonyl or $C_{1-16}$-alkylcarbonyloxy group wherein hydrogen atoms may be wholly or partially replaced by fluorine or chlorine atoms, such as the methoxycarbonyl, ethoxycarbonyl, propoxycarbonyl, isopropoxycarbonyl, butoxycarbonyl, tert.butoxycarbonyl, pentoxycarbonyl, hexoxycarbonyl, octyloxycarbonyl, nonyloxycarbonyl, decyloxycarbonyl, undecyloxycarbonyl, dodecyloxycarbonyl, hexadecyloxycarbonyl, methylcarbonyloxy, ethylcarbonyloxy, 2,2,2-trichloroethylcarbonyloxy, propylcarbonyloxy, isopropylcarbonyloxy, butylcarbonyloxy, tert.butylcarbonyloxy, pentylcarbonyloxy, hexylcarbonyloxy, octylcarbonyloxy, nonylcarbonyloxy, decylcarbonyloxy, undecylcarbonyloxy, dodecylcarbonyloxy or hexadecylcarbonyloxy group, a phenyl-$C_{1-6}$-alkoxycarbonyl group such as the benzyloxycarbonyl, phenylethoxycarbonyl or phenylpropoxycarbonyl group, a 3-amino-propionyl group wherein the amino group may be mono or disubstituted by $C_{1-6}$-alkyl or $C_{3-7}$-cycloalkyl groups and the substituents may be identical or different, a $C_{1-3}$-alkylsulphonyl-$C_{2-4}$-alkoxycarbonyl, $C_{1-3}$-alkoxy-$C_{2-4}$-alkoxy-$C_{2-4}$-alkoxycarbonyl, $R_a$—CO—O—$(R_bCR_c)$—O—CO, $C_{1-6}$-alkyl-CO—NH—$(R_dCR_e)$—O—CO or $C_{1-6}$-alkyl-CO—O—$(R_dCR_e)$—$(R_dCR_e)$—O—CO group wherein $R_a$ to $R_c$ are as hereinbefore defined, $R_d$ and $R_e$, which may be identical or different, denote hydrogen atoms or $C_{1-3}$-alkyl groups.

Moreover, the saturated alkyl and alkoxy moieties containing more than 2 carbon atoms mentioned in the definitions given above also include the branched isomers thereof, such as the isopropyl, tert.butyl, isobutyl group, etc.

Preferred compounds of the above general formula I are those wherein one of the groups m or n denotes the number 0 and the other group m or n denotes the number 1, Ar denotes a phenylene group optionally substituted by a fluorine, chlorine or bromine atom or by a methyl, hydroxy, methoxy or benzyloxy group, which may be substituted by another methyl group, $R_1$ denotes a phenyl group optionally substituted by a fluorine, chlorine or bromine atom or by a trifluoromethyl, aminosulphonyl, $C_{1-3}$-alkyl or $C_{1-3}$-alkoxy group, which may additionally be substituted by a fluorine, chlorine or bromine atom or by a trifluoromethyl, $C_{1-3}$-alkyl or $C_{1-3}$-alkoxy group, a methyl group substituted by a dimethylamino, pyrrolidino or imidazolyl group, wherein the imidazolyl moiety may be substituted by a methyl group, an amino, $C_{1-5}$-alkylamino, cyclopentylamino or benzylamino group which may be substituted at the amino-nitrogen atom by a carboxy-$C_{1-2}$-alkyl, $C_{1-3}$-alkoxycarbonyl-$C_{1-2}$-alkyl, carboxy-$C_{1-2}$-alkylcarbonyl or $C_{1-3}$-alkoxycarbonyl-$C_{1-2}$-alkylcarbonyl group, a benzoylamino or phenylsulphonylamino group, a cyclopropyl group which is substituted in the 1 position by a 5- to 7-membered cycloalkyleneiminocarbonyl group, an optionally methyl-substituted pyrrolidinocarbonyl, piperidinocarbonyl, pyrrolidinosulphonyl or piperidinosulphonyl group, a $C_{1-3}$-alkoxy group wherein the alkoxy moiety in the 2 or 3 position may be substituted in each case by an amino, $C_{1-3}$-alkylamino or di-($C_{1-3}$-alkyl)-amino group, a phenyl-$C_{1-3}$-alkoxy or pyridinyloxy group, a $C_{5-7}$-cycloalkoxy group wherein the methylene group in the 3 or 4 position may be replaced by an —NH group, whilst the —NH group may be substituted
by a $C_{1-3}$-alkyl or ($C_{2-3}$-alkanoyl group,
by a $C_{2-3}$-alkanoyl or aminocarbonyl group wherein in each case the oxygen atom of the carbonyl group is replaced by an imino group, $R_2$ denotes a hydrogen, fluorine, chlorine or bromine atom, a methyl, hydroxy or methoxy group, $R_3$ denotes a hydrogen atom or a methyl group, $R_4$ denotes a hydrogen atom or a methyl or ethyl group optionally substituted by a carboxy or $C_{1-3}$-alkoxycarbonyl group and $R_5$ denotes a cyano group or an amidino group optionally substituted by a $C_{1-6}$-alkoxycarbonyl or benzoyl group, the isomers thereof and the salts thereof.

Particularly preferred compounds of general formula I are those wherein one of the groups m or n denotes the number 0 and
the other group m or n denotes the number 1, Ar denotes a phenylene group optionally substituted by a methyl, hydroxy, methoxy or benzyloxy group, $R_1$ denotes a phenyl group optionally substituted by a fluorine, chlorine or bromine atom or by a trifluoromethyl, aminosulphonyl, $C_{1-3}$-alkyl or $C_{1-3}$-alkoxy group, which may additionally be substituted by a fluorine, chlorine or bromine atom or by a trifluoromethyl, $C_{1-3}$-alkyl or $C_{1-3}$-alkoxy group, a cyclopropyl group which is substituted in the 1 position by a 5- to 7-membered cycloalkyleneiminocarbonyl group, or a 4- to 7-membered cycloalkyleneiminocarbonyl group, an optionally methyl-substituted pyrrolidinocarbonyl, piperidinocarbonyl or pyrrolidinosulphonyl group, $R_2$ denotes a hydrogen, fluorine, chlorine or bromine atom or a methyl group, $R_3$ denotes a hydrogen atom or a methyl group, $R_4$ denotes a hydrogen atom or a methyl or ethyl group substituted by a carboxy, methoxycarbonyl or ethoxycarbonyl group and $R_5$ denotes an amidino group optionally substituted by a $C_{1-6}$-alkoxycarbonyl or benzoyl group, the isomers thereof and the salts thereof.

The following compounds may be mentioned by way of example:

(a) 2-(5-carbamimidoyl-2-hydroxy-phenyl)-N-[3-methyl-4-(pyrrolidin-1-yl-carbonyl)-phenyl]-acetamide, (b) 2-(2-benzyloxy-5-carbamimidoyl-phenyl)-N-(2-ethoxycarbonyl-ethyl)-N-[3-methyl-4-(pyrrolidin-1-yl-carbonyl)-phenyl]-acetamide, (c) 2-(2-hydroxy-5-carbamimidoyl-phenyl)-N-(2-ethoxycarbonylethyl)-N-[3-methyl-4-(pyrrolidin-1-yl-carbonyl)-phenyl]-acetamide, (d) 2-(2-hydroxy-5-carbamimidoyl-phenyl)-N-(2-carboxyethyl)-N-[3-methyl-4-(pyrrolidin-1-yl-carbonyl)-phenyl]-acetamide, (e) 2-(5-carbamimidoyl-2-hydroxy-phenyl)-N-[3-methyl-4-(piperidin-1-yl-carbonyl)-phenyl]-acetamide and (f) 2-(5-carbamimidoyl-2-hydroxy-phenyl)-N-[3-methyl-4-(2-aminosulphonyl-phenyl)-phenyl]-acetamide, wherein the amidino group may additionally be substituted by a $C_{1-6}$-alkoxycarbonyl or benzoyl group, and the salts thereof.

According to the invention, the compounds of general formula I are obtained by methods known per se, e.g. by the following processes:

a) acylation of a compound of general formula

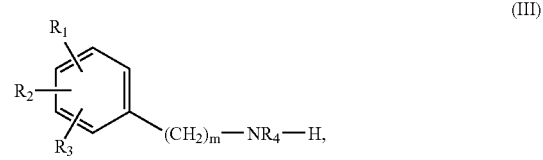

(III)

wherein
$R_1$ to $R_4$ and m are as hereinbefore defined, with a carboxylic acid of general formula

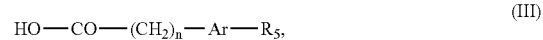

(III)

wherein
Ar, $R_5$ and n are as hereinbefore defined, or with the reactive derivatives thereof.

The acylation is conveniently carried out with a corresponding halide or anhydride in a solvent such as methylene chloride, chloroform, carbon tetrachloride, ether, tetrahydrofuran, dioxane, benzene, toluene, acetonitrile or sulpholane, optionally in the presence of an inorganic or organic base at temperatures between −20 and 200° C., but preferably at temperatures between −10 and 160° C.

The acylation may, however, also be carried out with the free acid, optionally in the presence of an acid-activating agent or a dehydrating agent, e.g. in the presence of isobutyl chloroformate, thionyl chloride, trimethylchlorosilane, hydrogen chloride, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/N-hydroxysuccinimide or 1-hydroxybenzotriazole, N,N'-carbonyldiimidazole or N,N'-thionyldiimidazole or triphenylphosphine/carbon tetrachloride, at temperatures between −20 and 200° C., but preferably at temperatures between −10 and 160° C.

b) In order to prepare a compound of general formula I wherein $R_5$ denotes an amidino group which may be substituted by one or two $C_{1-3}$-alkyl groups:
reaction of a compound of general formula

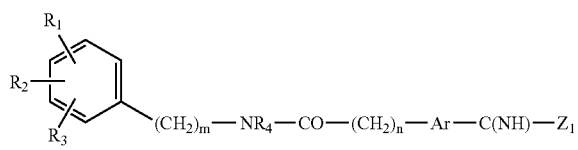

optionally formed in the reaction mixture wherein $R_1$ to $R_4$, Ar and n are as hereinbefore defined and $Z_1$ denotes an alkoxy or aralkoxy group such as the methoxy, ethoxy, n-propoxy, isopropoxy or benzyloxy group or an alkylthio or aralkylthio group such as the methylthio, ethylthio, n-propylthio or benzylthio group, with an amine of general formula

wherein $R_6$ and $R_7$, which may be identical or different, each denote a hydrogen atom or a $C_{1-3}$-alkyl group, or with the salts thereof.

The reaction is conveniently carried out in a solvent such as methanol, ethanol, n-propanol, tetrahydrofuran or dioxane at temperatures between 0 and 150° C., preferably at temperatures between 0 and 80° C., with an amine of general formula V or with a corresponding acid addition salt such as, for example, ammonium carbonate or ammonium acetate.

A compound of general formula IV is obtained, for example, by reacting a corresponding cyano compound with a corresponding alcohol such as methanol, ethanol, n-propanol, isopropanol or benzylalcohol in the presence of an acid such as hydrochloric acid or by reacting a corresponding amide with a trialkyloxonium salt such as triethyloxonium tetrafluoroborate in a solvent such as methylene chloride, tetrahydrofuran or dioxane at temperatures between 0 and 50° C., but preferably at 20° C., or a corresponding nitrile with hydrogen sulphide, conveniently in a solvent such as pyridine or dimethylformamide and in the presence of a base such as triethylamine, and subsequently alkylating the thioamide formed with a corresponding alkyl or aralkyl halide.

If according to the invention a compound of general formula I is obtained which contains an amino or imino group, this can subsequently be converted with a corresponding acyl derivative into a corresponding acyl compound of general formula I, and/or if a compound of general formula I is obtained which contains an esterified carboxy group, this can be converted by hydrolysis into a corresponding carboxylic acid of general formula I, and/or if a compound of general formula I is obtained which contains a carboxy group, this can be converted by esterification into a corresponding ester.

The subsequent acylation is conveniently carried out with a corresponding halide or anhydride in a solvent such as methylene chloride, chloroform, carbon tetrachloride, ether, tetrahydrofuran, dioxane, benzene, toluene, acetonitrile or sulpholane, optionally in the presence of an inorganic or organic base at temperatures between −20 and 200° C., but preferably at temperatures between −10 and 160° C. This may also, however, be carried out with the free acid, optionally in the presence of an acid-activating agent or a dehydrating agent, e.g. in the presence of isobutyl chloroformate, thionyl chloride, trimethylchlorosilane, hydrogen chloride, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/N-hydroxysuccinimide or 1-hydroxy-benzotriazole, N,N'-carbonyldiimidazole or N,N'-thionyldiimidazole or triphenylphosphine/carbon tetrachloride, at temperatures between −20 and 200° C., but preferably at temperatures between −10 and 160° C.

The subsequent hydrolysis is conveniently carried out either in the presence of an acid such as hydrochloric acid, sulphuric acid, phosphoric acid, acetic acid, trichloroacetic acid, trifluoroacetic acid or mixtures thereof or in the presence of a base such as lithium hydroxide, sodium hydroxide or potassium hydroxide in a suitable solvent such as water, water/methanol, water/ethanol, water/isopropanol, methanol, ethanol, water/tetrahydrofuran or water/dioxane and the subsequent decarboxylation is carried out in the presence of an acid as hereinbefore described at temperatures between −10 and 120° C., e.g. at temperatures between ambient temperature and the boiling temperature of the reaction mixture.

The subsequent esterification is carried out with a corresponding alcohol, conveniently in a solvent or mixture of solvents such as methylene chloride, benzene, toluene, chlorobenzene, tetrahydrofuran, benzene/tetrahydrofuran or dioxane, but preferably in an excess of the alcohol used, optionally in the presence of an acid such as hydrochloric acid or in the presence of a dehydrating agent, e.g. in the presence of isobutyl chloroformate, thionyl chloride, trimethylchlorosilane, hydrochloric acid, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/N-hydroxysuccinimide, N,N'-carbonyldiimidazole or N,N'-thionyldiimidazole, triphenylphosphine/carbon tetrachloride or triphenylphosphine/diethyl azodicarboxylate optionally in the presence of a base such as potassium carbonate, N-ethyl-diisopropylamine or N,N-dimethylamino-pyridine conveniently at temperatures between 0 and 150° C., preferably at temperatures between 0 and 80° C., or with a corresponding halide in a solvent such as methylene chloride, tetrahydrofuran, dioxane, dimethylsulphoxide, dimethylformamide or acetone optionally in the presence of a reaction accelerator such as sodium or potassium iodide and preferably in the presence of a base such as sodium carbonate or potassium carbonate or in the presence of a tertiary organic base such as N-ethyl-diisopropylamine or N-methyl-morpholine, which may simultaneously serve as solvent, or optionally in the presence of silver carbonate or silver oxide at temperatures between −30 and 100° C., but preferably at temperatures between −10 and 80° C.

In the reactions described hereinbefore, any reactive groups present such as hydroxy, carboxy, amino, alkylamino or imino groups may be protected during the reaction by conventional protecting groups which are cleaved again after the reaction.

For example, a protecting group for a hydroxy group may be a methoxy, benzyloxy, trimethylsilyl, acetyl, benzoyl, tert.butyl, trityl, benzyl or tetrahydropyranyl group, protecting groups for a carboxy group may be a trimethylsilyl, methyl, ethyl, tert.butyl, benzyl or tetrahydropyranyl group and protecting groups for an amino, alkylamino or imino group may be an acetyl, trifluoroacetyl, benzoyl, ethoxycarbonyl, tert.butoxycarbonyl, benzyloxycarbonyl, benzyl, methoxybenzyl or 2,4-dimethoxybenzyl group and additionally, for the amino group, a phthalyl group.

Any protecting group used is optionally subsequently cleaved for example by hydrolysis in an aqueous solvent, e.g. in water, isopropanol/water, tetrahydrofuran/water or dioxan/water, in the presence of an acid such as trifluoroacetic acid, hydrochloric acid or sulphuric acid or in the presence of an alkali metal base such as lithium hydroxide, sodium hydroxide or potassium hydroxide or by ether splitting, e.g. in the presence of iodotrimethylsilane, at temperatures between 0 and 100° C., preferably at temperatures between 10 and 50° C.

However, a benzyl, methoxybenzyl or benzyloxycarbonyl group is cleaved, for example, hydrogenolytically, e.g. with hydrogen in the presence of a catalyst such as palladium/charcoal in a solvent such as methanol, ethanol, ethyl acetate, dimethylformamide, dimethylformamide/acetone or glacial acetic acid, optionally with the addition of an acid such as hydrochloric acid at temperatures between 0 and 50° C., but preferably at ambient temperature, and at a hydrogen pressure of 1 to 7 bar, but preferably 3 to 5 bar.

A methoxybenzyl group may also be cleaved in the presence of an oxidising agent such as cerium(IV)ammonium nitrate in a solvent such as methylene chloride, acetonitrile or acetonitrile/water at temperatures between 0 and 50° C., but preferably at ambient temperature.

A methoxy may conveniently be cleaved in the presence of boron tribromide in a solvent such as methylene chloride at temperatures between −35 and −25° C.

A 2,4-dimethoxybenzyl group, however, is preferably cleaved in trifluoroacetic acid in the presence of anisol.

A tert.butyl or tert.butyloxycarbonyl group is preferably cleaved by treating with an acid such as trifluoroacetic acid or hydrochloric acid or by treating with iodotrimethylsilane, optionally using a solvent such as methylene chloride, dioxan, methanol or diethylether.

A phthalyl group is preferably cleaved in the presence of hydrazine or a primary amine such as methylamine, ethylamine or n-butylamine in a solvent such as methanol, ethanol, isopropanol, toluene/water or dioxan at temperatures between 20 and 50° C.

An allyloxycarbonyl group is cleaved by treating with a catalytic amount of tetrakis-(triphenylphosphine)-palladium (O), preferably in a solvent such as tetrahydrofuran and preferably in the presence of an excess of a base such as morpholine or 1,3-dimedone at temperatures between 0 and 100° C., preferably at ambient temperature and under inert gas, or by treating with a catalytic amount of tris-(triphenylphosphine)-rhodium(I)chloride in a solvent such as aqueous ethanol and optionally in the presence of a base such as 1,4-diazabicyclo[2.2.2]octane at temperatures between 20 and 70° C.

The compounds of general formulae II to V used as starting materials, some of which are known from the literature, are obtained by methods known from the literature, and furthermore their preparation is described in the Examples.

The chemistry of the compounds of general formula II is described, for example, by Schröter in Stickstoffverbindungen [Nitrogen compounds] II, pages 341-730, Methoden der organischen Chemie (Houben-Weyl), 4$^{th}$ edition, published by Thieme, Stuttgart 1957, and those of general formula III are described by J. F. Hartwig in Angew. Chem. 110, 2154-2157 (1998).

Moreover, the compounds of general formula I obtained may be resolved into their enantiomers and/or diastereomers.

Thus, for example, the compounds of general formula I obtained which occur as racemates may be separated by methods known per se (cf. Allinger N. L. and Eliel E. L. in "Topics in Stereochemistry", Vol. 6, Wiley Interscience, 1971) into their optical enantiomers and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)- or (−)-menthyloxycarbonyl.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, if the new compounds of formula I contain a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, cyclohexylamine, ethanolamine, diethanolamine and triethanolamine.

As already mentioned, the new compounds of general formula I and the salts thereof have valuable properties. Thus, the compounds of general formula I wherein $R_5$ denotes a cyano group are valuable intermediate products for preparing the other compounds of general formula I and the compounds of general formula I wherein $R_5$ denotes one of the above-mentioned amidino groups and the tautomers, the stereoisomers and the physiologically acceptable salts thereof have valuable pharmacological properties, particularly an antithrombotic activity which is preferably based on an effect on thrombin or factor Xa, on a prolonging effect on aPTT time and on an inhibitory effect on related serine proteases such as e.g. trypsin, urokinase factor VIIa, factor IX, factor XI and factor XII.

For example, the compounds

A=2-(5-carbamimidoyl-2-hydroxy-phenyl)-N-[3-methyl-4-(pyrrolidin-1-yl-carbonyl)-phenyl]-acetamide-hydrochloride, B=2-(2-benzyloxy-5-carbamimidoyl-phenyl)-N-(2-ethoxycarbonyl-ethyl)-N-[3-methyl-4-(pyrrolidin-1-yl-carbonyl)-phenyl]-acetamide-hydrochloride, C=2-(2-hydroxy-5-carbamimidoyl-phenyl)-N-(2-ethoxycarbonyl-ethyl)-N-[3-methyl-4-(pyrrolidin-1-yl-carbonyl)-phenyl]-acetamide-hydrochloride, D=2-(2-hydroxy-5-carbamimidoyl-phenyl)-N-(2-carboxyethyl)-N-[3-methyl-4-(pyrrolidin-1-yl-carbonyl)-phenyl]-acetamide-hydrochloride E=2-(5-carbamimidoyl-2-hydroxy-phenyl)-N-[3-methyl-4-(piperidin-1-yl-carbonyl)-phenyl]-acetamide-hydrochloride and F=2-(5-carbamimidoyl-2-hydroxy-phenyl)-N-[3-methyl-4-(2-aminosulphonyl-phenyl)-phenyl]-acetamide-hydrochloride, were investigated for their effect on the inhibition of factor Xa as follows:

Method: Enzyme-kinetic measurement with chromogenic substrate. The quantity of anpnitroaniline (pNA) released from the colourless chromogenic substrate by human factor Xa is determined photometrically at 405 nm. It is proportional to the activity of the enzyme used. The inhibition of the enzyme activity by the test substance I (in relation to the solvent control) is determined at various concentrations of test substance and from this the $IC_{50}$ is calculated, as the concentration which inhibits the factor Xa used by 50%.

Material:

Tris(hydroxymethyl)-aminomethane buffer (100 mmol) of and sodium chloride (150 mMol), pH 8.0

Factor Xa (Roche), spec. activity: 10 U/0.5 ml, final concentration: 0.175 U/ml per reaction mixture Substrate Chromozym X (Roche), final concentration: 200 µMol/l per reaction mixture Test substance: final concentration 100, 30, 10, 3, 1, 0.3, 0.1, 0.03, 0.01, 0.003, 0.001 µMol/l Procedure: 10 µl of a 23.5-times concentrated starting solution of the test substance or solvent (control), 175 µl of tris (hydroxymethyl)-aminomethane buffer and 25 µl of Factor Xa working solution of 1.65 U/ml are incubated for 10 minutes at 37° C. After the addition of 25 µl of Chromozym X working solution (1.88 µMol/l) the sample is measured in a photometer (SpectraMax 250) at 405 nm for 150 seconds at 37° C.

Evaluation:
1. Determining the maximum increase (deltaOD/minutes) over 3 measuring points.
2. Determining the % inhibition based on the solvent control.
3. Plotting a dosage/activity curve (% inhibition vs substance concentration).
4. Determining the $IC_{50}$ by interpolating the X value (substance concentration) of the dosage/activity curve at Y=50% inhibition.

The following Table shows the results obtained:

| substance | inhibition of factor Xa ($IC_{50}$ in µM) |
|---|---|
| A | 0.030 |
| B | 0.680 |
| C | 0.120 |
| D | 0.850 |
| E | 0.085 |
| F | 0.260 |

The compounds prepared according to the invention are well tolerated, as no toxic side effects could be observed at therapeutic doses.

In view of their pharmacological properties the new compounds and the physiologically acceptable salts thereof are suitable for the prevention and treatment of venous and arterial thrombotic diseases, such as for example the treatment of deep leg vein thrombosis, for preventing reocclusions after bypass operations or angioplasty (PT(C)A), and occlusion in peripheral arterial diseases such as pulmonary embolism, disseminated intravascular coagulation, for preventing coronary thrombosis, stroke and the occlusion of shunts. In addition, the compounds according to the invention are suitable for antithrombotic support in thrombolytic treatment, such as for example with rt-PA or streptokinase, for preventing long-term restenosis after PT(C)A, for preventing metastasis and the growth of clot-dependent tumours and fibrin-dependent inflammatory processes, e.g. in the treatment of pulmonary fibrosis.

The dosage required to achieve such an effect is appropriately 0.1 to 30 mg/kg, preferably 0.3 to 10 mg/kg by intravenous route, and 0.1 to 50 mg/kg, preferably 0.3 to 30 mg/kg by oral route, in each case administered 1 to 4 times a day. For this purpose, the compounds of formula I prepared according to the invention may be formulated, optionally together with other active substances, with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The Examples which follow are intended to illustrate the invention:

EXAMPLE 1

2-(3-carbamimidoyl-phenyl)-N-[2-chloro-5-(1-(pyrrolidin-1-yl-carbonyl)-cyclopropyl)-phenyl]-acetamide-hydrochloride a. 1-(4-chloro-3-nitro-phenyl)-cyclopropanecarboxylic acid 350 ml of fuming nitric acid are combined at −25 to −30° C. with 50.0 g (0.21 mol) of 1-(4-chloro-phenyl)-cyclopropanecarboxylic acid in batches. After it has all been added the mixture is stirred for a further 15 minutes at −25° C. and then poured onto ice. The substance precipitated is suction filtered, washed with water and dried.

Yield: 58.5 g (95% of theory), $R_f$ value: 0.43 (silica gel; methylene chloride/methanol=9.5:0.5)

b. 5-[1-(pyrrolidin-1-yl-carbonyl)-cyclopropyl]-2-chloro-nitrobenzene 2.4 g (0.01 mol) of 1-(4-chloro-3-nitro-phenyl)-cyclopropanecarboxylic acid are dissolved in 25 ml of tetrahydrofuran and after the addition of 3.2 g (0.01 mol) of O-(benzotriazol-1-yl)-N,N,N',N'-tetramethyluronium tetrafluoroborate, 1.1 ml of (0.01 mol) of N-methyl-morpholine and 1.0 ml of (0.012 mol) of pyrrolidine stirred for 16 hours at ambient temperature. The solvent is distilled off, the residue is poured onto ice water, made alkaline with ammonia and extracted with ethyl acetate. The organic phase is dried and evaporated down.

Yield: 2.5 g (85% of theory), $R_f$ value: 0.18 (silica gel; cyclohexane/ethyl acetate=1:1)

c. 5-[1-(pyrrolidin-1-yl-carbonyl)-cyclopropyl]-2-chloro-aniline 1.8 g (8.14 mmol) of 5-[1-(pyrrolidin-1-yl-carbonyl)-cyclopropyl]-2-chloro-nitrobenzene are dissolved in 30 ml of ethyl acetate and 30 ml of ethanol and after the addition of 0.8 g palladium on active charcoal (10%) hydrogenated for 3 hours at ambient temperature with hydrogen. Then the catalyst is filtered off and the filtrate is evaporated down.

Yield: 2.0 g (92.8% of theory), $R_f$ value: 0.24 (silica gel; cyclohexane/ethyl acetate/ammonia=1:1:0.01) $C_{14}H_{17}ClN_2O$ (264.75) mass spectrum: $M^+$=264/6 (Cl)

d. 2-(3-cyano-phenyl)-N-[2-chloro-5-(1-(pyrrolidin-1-yl-carbonyl)-cyclopropyl)-phenyl]-acetamide Prepared analogously to Example 1b from 5-[1-(pyrrolidin-1-yl-carbonyl)-cyclopropyl]-2-chloro-aniline, O-(benzotriazol-1-yl)-N,N,N',N'-tetramethyluronium tetrafluoroborate, N-methyl-morpholine and 3-cyanophenylacetic acid in dimethylformamide.

Yield: 43% of theory, $R_f$ value: 0.21 (silica gel; cyclohexane/ethyl acetate=1:2)

e. 2-(3-carbamimidoyl-phenyl)-N-[2-chloro-5-(1-(pyrrolidin-1-yl-carbonyl)-cyclopropyl)-phenyl]-acetamide-hydrochloride 400 mg (0.1 mmol) of 2-(3-cyano-phenyl)-N-[2-chloro-5-(1-(pyrrolidin-1-yl-carbonyl)-cyclopropyl)-phenyl]-acetamide are dissolved in 60 ml of saturated ethanolic hydrochloric acid and stirred for 17 hours at ambient temperature. The solvent is distilled off, the residue is dissolved in 50 ml of absolute ethanol and mixed with 1.5 g (15.6 mmol) of ammonium carbonate. After 22 hours at ambient temperature the mixture is evaporated to dryness. The residue is chromatographed on silica gel, eluting with methylene chloride/methanol/glacial acetic acid (9:1:0.01).

Yield: 50 mg (11% of theory), $R_f$ value: 0.59 (silica gel; methylene chloride/methanol/ammonia=4:1:0.01) $C_{23}H_{25}ClN_4O_2 \times HCl$ (424.94/461.4) mass spectrum: $(M+H)^+$=425/7 (Cl)

EXAMPLE 2

3-carbamimidoyl-N-[3-(1-(pyrrolidin-1-yl-carbonyl)-cyclopropyl)-benzyl]-benzamide-hydrochloride a. 1-(3-bromo-phenyl)-1-cyclopropane-nitril 25 g (0.13 mol) of 3-bromo-benzylcyanide are taken up in 32 ml (0.38 mol) of 1-bromo-2-chloro-ethane and combined with 0.6 g (2.6 mmol) of benzyltriethylammonium chloride. Then a solution of 105.8 g (2.65 mol) of sodium hydroxide in 106 ml of water is added dropwise at 10 to 25° C. After 20 hours at 55° C. the reaction solution is poured onto ice water and extracted with ethyl acetate. The organic extracts are dried and evaporated down. The residue is triturated with petroleum ether, suction filtered and dried.

Yield: 19.3 g (68% of theory), $R_f$ value: 0.69 (petroleum ether/ethyl acetate=4:1)

b. 1-(3-bromo-phenyl)-cyclopropanecarboxylic acid 7.6 g (0.135 mol) of potassium hydroxide are dissolved in 60 ml of ethyleneglycol, combined batchwise with 10.0 g (0.045 mol) of 1-(3-bromo-phenyl)-1-cyclopropane-nitrile and after the addition of 30 ml of water heated to 140° C. for 4.5 hours. After cooling it is poured onto 600 ml of ice water and extracted with ether. The aqueous phase is poured onto ice/conc. hydrochloric acid, the product precipitated is suction filtered and dried.

Yield: 10.1 g (93% of theory), $R_f$ value: 0.85 (silica gel; cyclohexane/ethyl acetate/glacial acetic acid=1:1:0.01)

c. 3-[1-(pyrrolidin-1-yl-carbonyl)-cyclopropyl]-bromo-benzene

Prepared analogously to Example 1b from 1-(3-bromophenyl)-cyclopropanecarboxylic acid, pyrrolidine, O-(benzotriazol-1-yl)-N,N,N',N'-tetramethyluronium tetrafluoroborate and N-methyl-morpholine in tetrahydrofuran.

Yield: 98% of theory, $R_f$ value: 0.55 (silica gel; cyclohexane/ethyl acetate/glacial acetic acid=1:1:0.01)

d. 3-[1-(pyrrolidin-1-yl-carbonyl)-cyclopropyl]-benzonitrile 6 g (20.4 mmol) of 3-[1-(pyrrolidin-1-yl-carbonyl)-cyclopropyl]-bromo-benzene are dissolved in 25 ml of dimethylformamide and after the addition of 2.7 g (30.6 mmol) of copper-I-cyanide, 0.3 g (0.216 mmol) of tetrakis-triphenylphosphine-palladium-(0) and 5 g of aluminium oxide stirred for 30 hours at 140° C. The insoluble matter is filtered off and the solution is evaporated down. The residue is chromatographed on silica gel, eluting with cyclohexane/ethyl acetate (1:2).

Yield: 1.8 g (36% of theory), $R_f$ value: 0.32 (silica gel; cyclohexane/ethyl acetate/glacial acetic acid=1:1:0.01)

e. 3-[1-(pyrrolidin-1-yl-carbonyl)-cyclopropyl]-benzylamine 1.8 g (7.5 mmol) of 3-[1-(pyrrolidin-1-yl-carbonyl)-cyclopropyl]-benzonitrile are hydrogenated with hydrogen in 50 ml of methanolic ammonia with the addition of 300 mg Raney nickel for 3 hours at 70° C. Then the catalyst is filtered off and the filtrate is evaporated down.

Yield: 1.8 g (98% of theory), $R_f$ value: 0.94 (silica gel; methylene chloride/methanol/ammonia=4:1:0.01)

f. 3-cyano-N-[3-(1-(pyrrolidin-1-yl-carbonyl)-cyclopropyl)-benzyl]-benzamide

Prepared analogously to Example 1b from 3-[1-(pyrrolidin-1-yl-carbonyl)-cyclopropyl]-benzylamine, 3-cyanobenzoic acid, O-(benzotriazol-1-yl)-N,N,N',N'-tetramethyluronium tetrafluoroborate and N-methyl-morpholine in tetrahydrofuran.

Yield: 96% of theory, $R_f$ value: 0.56 (silica gel; ethyl acetate/ethanol=9:1)

g. 3-carbamimidoyl-N-[3-(1-(pyrrolidin-1-yl-carbonyl)-cyclopropyl)-benzyl]-benzamide-hydrochloride Prepared analogously to Example 1e from 3-cyano-N-[3-(1-(pyrrolidin-1-yl-carbonyl)-cyclopropyl)-benzyl]-benzamide and hydrochloric acid/ammonium carbonate in ethanol.

Yield: 58% of theory, $R_f$ value: 0.19 (Reversed phase RP 8; 5% sodium chloride solution/methanol=1:1) $C_{23}H_{26}N_4O_2 \times HCl$ (390.48/426.95) mass spectrum: $(M+H)^+$=391 $(M-H+HCl)^-$=425/7 (Cl)

The following compounds are prepared analogously to Example 2:

(1) 3-carbamimidoyl-N-[4-(1-(pyrrolidin-1-yl-carbonyl)-cyclopropyl)-benzyl]-benzamide-hydrochloride Yield: 68% of theory, $C_{23}H_{26}N_4O_2 \times HCl$ (390.48/426.95) mass spectrum: $(M+H)^+$=391 $(M+2H)^{++}$=196

(2) 5-carbamimidoyl-2-hydroxy-N-[3-methyl-4-(pyrrolidin-1-yl-carbonyl)-benzyl]-benzamide-hydrochloride Yield: 34% of theory, $R_f$ value: 0.1 (Reversed phase RP8; 5% saline solution/methanol=1:1) $C_{21}H_{24}N_4O_3 \times HCl$ (380.46/416.91) mass spectrum: $(M+H)^+$=381 $(M-H)^-$=379

EXAMPLE 3

2-(5-carbamimidoyl-2-hydroxy-phenyl)-N-[2-methyl-5-(-(pyrrolidin-1-carbonyl)-cyclopropyl)-phenyl]-acetamide-hydrochloride a. 5-cyano-2-methoxy-phenylacetic acid Prepared analogously to Example 2d from 5-bromo-2-methoxy-phenylacetic acid, copper-I-cyanide, tetrakis-triphenylphosphine-palladium-(0) and aluminium oxide in dimethylformamide.

Yield: 37% of theory, $R_f$ value: 0.26 (silica gel; cyclohexane/ethyl acetate/glacial acetic acid=1:1:0.01)

b. 2-(5-cyano-2-methoxy-phenyl)-N-[2-methyl-5-(1-(pyrrolidin-1-carbonyl)-cylopropyl)-phenyl]-acetamide 0.6 g (3.3 mmol) of 5-cyano-2-methoxy-phenylacetic acid are dissolved in 10 ml of dimethylformamide and after the addition of 0.5 g (3.3 mmol) of N,N-carbonyldiimidazole stirred for 10 minutes at ambient temperature. Then 0.8 g (3.3 mmol) of 5-(pyrrolidin-1-yl-carbonyl)-cyclopropyl)-2-methyl-aniline are added. The reaction mixture is stirred for 4 hours at 80° C., cooled to ambient temperature, combined with ice water, made alkaline with ammonia and extracted several times with ethyl acetate. The combined organic extracts are dried and evaporated down. The residue is chromatographed on silica gel, eluting with cyclohexane/ethyl acetate (7:3).

Yield: 73% of theory, $R_f$ value: 0.30 (silica gel; ethyl acetate)

c. 2-(5-cyano-2-hydroxy-phenyl)-N-[2-methyl-5-(1-(pyrrolidin-1-carbonyl)-cyclopropyl)-phenyl]-acetamide 0.7 g (1.67 mmol) of 2-(5-cyano-2-methoxy-phenyl)-N-[2-methyl-5-(1-(pyrrolidin-1-carbonyl)-cyclopropyl)-phenyl]-acetamide are dissolved in 35 ml of methylene chloride and at −35 to −25° C. 10 ml of a 1-molar solution of boron tribromide in methylene chloride (10 mmol) are added dropwise. After 1 hour's stirring at 20° C., first ice is added, then 20 ml of 2N hydrochloric acid. The aqueous phase is extracted several times with methylene chloride, the combined organic extracts are dried and evaporated down. The residue is chromatographed on silica gel, eluting with methylene chloride/ethanol (100:1).

Yield: 81% of theory, $R_f$ value: 0.14 (silica gel; methylene chloride/ethanol=49:1)

d. 2-(5-carbamimidoyl-2-hydroxy-phenyl)-N-[2-methyl-5-(1-(pyrrolidin-1-carbonyl)-cyclopropyl)-phenyl]-acetamide-hydrochloride Prepared analogously to Example 1e from 2-(5-cyano-2-hydroxy-phenyl)-N-[2-methyl-5-(1-(pyrrolidin-1-carbonyl)-cyclopropyl)-phenyl]-acetamide, and hydrochloric acid/ammonium carbonate in ethanol.

Yield: 80% of theory, $R_f$ value: 0.39 (silica gel; methylene chloride/methanol/glacial acetic acid=4:1:0.01) $C_{24}H_{28}N_4O_3 \times HCl$ (420.51/456.98) mass spectrum: $(M+H)^+=421$ $(M+Cl)^-=455/7$ (Cl)

The following compound is prepared analogously to Example 3:

(1) 2-(5-carbamimidoyl-2-methoxy-phenyl)-N-[2-methyl-5-(1-(pyrrolidin-1-carbonyl)-cyclopropyl)-phenyl]-acetamide-hydrochloride Yield: 92% of theory, $R_f$ value: 0.33 (silica gel; methylene chloride/methanol/glacial acetic acid=4:1:0.01) $C_{25}H_{30}N_4O_3 \times HCl$ (434.55/471.01) mass spectrum: $(M+H)^+=435$

EXAMPLE 4

2-(5-carbamimidoyl-2-hydroxy-phenyl)-N-[3-methyl-4-(pyrrolidin-1-yl-carbonyl)-phenyl]-acetamide-hydrochloride a. 2-(5-cyano-2-methoxy-phenyl)-N-[3-methyl-4-(pyrrolidin-1-yl-carbonyl)-phenyl]-acetamide 0.4 g (2 mmol) of 3-methyl-4-(pyrrolidin-1-yl-carbonyl)-aniline are dissolved in 15 ml of tetrahydrofuran and after the addition of 0.3 ml (2 mmol) of triethylamine and 0.4 g (2 mmol) of 5-cyano-3-methoxy-phenylacetic acid chloride stirred for 48 hours at ambient temperature. Then the mixture is combined with water, made alkaline with ammonia and extracted with ethyl acetate. The combined organic extracts are washed with 1N hydrochloric acid, dried and evaporated down.

Yield: 0.45 g (59% of theory), $R_f$ value: 0.18 (silica gel; ethyl acetate)

b. 2-(5-carbamimidoyl-2-methoxy-phenyl)-N-[3-methyl-4-(pyrrolidin-1-yl-carbonyl)-phenyl]-acetamide-hydrochloride Prepared analogously to Example 1e from 2-(5-cyano-2-methoxyphenyl)-N-[3-methyl-4-(pyrrolidin-1-yl-carbonyl)-phenyl]-acetamide and hydrochloric acid/ammonium carbonate in ethanol.

Yield: 36% of theory, $R_f$ value: 0.33 (Reversed phase RP 8; 5% sodium chloride solution/methanol=1:1) $C_{22}H_{26}N_4O_3 \times HCl$ (394.48/430.94) mass spectrum: $(M+H)^+=395$ $(M-H+HCl)^-=429$ c. 2-(5-carbamimidoyl-2-hydroxy-phenyl)-N-[3-methyl-4-(pyrrolidin-1-yl-carbonyl)-phenyl]-acetamide-hydrochloride Prepared analogously to Example 3c from 2-(5-carbamimidoyl-2-methoxy-phenyl)-N-[3-methyl-4-(pyrrolidin-1-yl-carbonyl)-phenyl]-acetamide-hydrochloride and boron tribromide in dichloromethane.

Yield: 19% of theory, $R_f$ value: 0.38 (Reversed phase RP 8; 5% sodium chloride solution/methanol=1:1) $C_{21}H_{24}N_4O_3 \times HCl$ (380.45/416.91) mass spectrum: $(M+H)^+=381$ $(M-H)^-=379$ The following compounds are prepared analogously to Example 4:

(1) 2-(3-carbamimidoyl-phenyl)-N-[3-methyl-4-(pyrrolidin-1-yl-carbonyl)-phenyl]-acetamide-hydrochloride Yield: 12% of theory, $C_{21}H_{24}N_4O_2 \times HCl$ (364.45/400.92) mass spectrum: $(M+H)^+=365$ (2) 2-(5-carbamimidoyl-2-hydroxy-phenyl)-N-methyl-N-[3-methyl-4-(pyrrolidin-1-yl-carbonyl)-phenyl]-acetamide-hydrochloride Yield: 99% of theory, $C_{22}H_{26}N_4O_3 \times HCl$ (394.48/430.94) mass spectrum: $(M+H)^+=395$ $(M-H)^-=393$ (3) 2-(5-carbamimidoyl-2-benzyloxy-phenyl)-N-methyl-N-[3-methyl-4-(pyrrolidin-1-yl-carbonyl)-phenyl]-acetamide-hydrochloride Yield: 90% of theory, $C_{29}H_{32}N_4O_3 \times HCl$ (484.60/521.06) mass spectrum: $(M+H)^+=485$ $(M-H+HCl)^-=519/21$ (Cl)

(4) 2-(5-carbamimidoyl-2-hydroxy-phenyl)-N-[3-methyl-4-(N-(3-ethoxycarbonyl-propionyl)-N-cyclopentyl-amino)-phenyl]-acetamide-hydrochloride Yield: 74% of theory, $C_{27}H_{34}N_4O_5 \times HCl$ (494.61/531.06) $R_f$ value: 0.36 (Reversed phase RP8; 5% saline solution/methanol=4:6) mass spectrum: $(M+H)^+=495$ $(M+Cl)^-=529/531$ (Cl $(M-H)^-=493$ (5) 2-(5-carbamimidoyl-2-benzyloxy-phenyl)-N-[3-methyl-4-(N-(3-ethoxycarbonyl-propionyl-N-(2-methyl-propyl)-amino)-phenyl]-acetamide-hydrochloride Yield: 74% of theory, $R_f$ value: 0.21 (silica gel; methylene chloride/ethanol=4:1) $C_{33}H_{40}N_4O_5 \times HCl$ (572.71/609.18) mass spectrum: $(M+H)^+=573$ $(M-H)^-=571$ (6) 2-(5-carbamimidoyl-2-hydroxy-phenyl)-N-[3-methyl-4-(N-(3-ethoxycarbonyl-propionyl)-N-(2-methyl-propyl)-amino)-phenyl]-acetamide-hydrochloride Yield: 100% of theory, $R_f$ value: 0.33 (Reversed phase RP8; 5% saline solution/methanol=4:6) $C_{26}H_{34}N_4O_5 \times HCl$ (482.58/519.05) mass spectrum: $(M+H)^+=483$ $(M-H)^-=481$ $(M+Cl)^-=517/519$ (Cl)

(7) 2-(5-carbamimidoyl-2-hydroxy-phenyl)-N-[3-methyl-4-(N-ethoxycarbonylacetyl-N-cyclopentyl-amino)-phenyl]-acetamide-hydrochloride (8) 2-(5-carbamimidoyl-2-hydroxy-phenyl)-N-[3-methyl-4-(pyrrolidin-1-yl-sulphonyl)-phenyl]-acetamide-hydrochloride

EXAMPLE 5

2-(5-carbamimidoyl-2-hydroxy-phenyl)-N-[2,5-dimethyl-4-(pyrrolidin-1-yl-carbonyl)-phenyl]-acetamide-hydrochloride a. 2,5-dimethyl-4-(pyrrolidin-1-yl-carbonyl)-bromobenzene Prepared analogously to Example 1b from 4-bromo-3,5-dimethyl-benzoic acid, pyrrolidine, O-(benzotriazol-1-yl)-N,N,N',N'-tetramethyluronium tetrafluoroborate and triethylamine in dimethylformamide.

Yield: 63% of theory, $R_f$ value: 0.45 (silica gel; methylene chloride/ethanol=19:1)

b. 2,5-dimethyl-4-(pyrrolidin-1-yl-carbonyl)-benzylaniline 2.3 g (0.01 mol) of 2,5-dimethyl-4-(pyrrolidin-1-yl-carbonyl)-bromobenzene and 1.3 g (0.012 mol) of benzylamine are dissolved in 25 ml of toluene and after the addition of 4.6 g of caesium carbonate, 100 mg palladium-II-acetate and 200 mg 2,2'-bis(diphenylphosphino)-1,1'-binaphthyl stirred for 7 hours under an argon atmosphere at 100° C. After cooling the mixture is diluted with ice water and extracted with ethyl acetate. The combined organic extracts are dried and evaporated down. The residue is chromatographed on silica gel, eluting with methylene chloride/ethanol (50:1 and 25:1).

Yield: 60% of theory, $R_f$ value: 0.30 (silica gel; methylene chloride/ethanol=9:1)

c. 2,5-dimethyl-4-(pyrrolidin-1-yl-carbonyl)-aniline

Prepared analogously to Example 1c from 2,5-dimethyl-4-(pyrrolidin-1-yl-carbonyl)-benzylaniline and palladium on active charcoal in methanol.

Yield: 94% of theory, $R_f$ value: 0.30 (silica gel; ethyl acetate/petroleum ether=1:1)

d. 2-benzyloxy-5-bromo-phenylacetic acid

A solution of 12.4 g (0.053 mol) of 2-hydroxy-5-bromo-phenylacetic acid in 125 ml of dimethylformamide is combined with 14 g (0.125 mol) of potassium tert.butoxide. After 15 minutes at ambient temperature 18.5 g (0.108 mol) of benzylbromide are added. The reaction solution is stirred for 3 hours at ambient temperature, poured onto ice water and extracted with ethyl acetate. The combined organic extracts are dried and evaporated down. The residue is dissolved in 100 ml of ethanol and after the addition of 50 ml of 2N sodium hydroxide solution stirred for 3 hours at ambient temperature. The solvent is distilled off, the residue is adjusted to pH 4 with 2N hydrochloric acid. After extraction with ethyl acetate the organic phases are dried and evaporated down. The residue is chromatographed on silica gel and eluted with petroleum ether/ethyl acetate (8:2).

Yield: 6.7 g (38% of theory), $R_f$ value: 0.50 (silica gel; ethyl acetate/petroleum ether=1:1)

e. 2-benzyloxy-5-cyano-phenylacetic acid

Prepared analogously to Example 2d from 2-benzyloxy-5-bromo-phenylacetic acid, copper-I-cyanide, tetrakis-triphenylphosphine-palladium-(0) and aluminium oxide in dimethylformamide.

Yield: 26% of theory, $R_f$ value: 0.45 (silica gel; methylene chloride/ethanol=19:1)

f. 2-(5-cyano-2-benzyloxy-phenyl)-N-[2,5-dimethyl-4-(pyrrolidin-1-yl-carbonyl)-phenyl]-acetamide Prepared analogously to Example 1b from 2-benzyloxy-5-cyano-phenylacetic acid, 2,5-dimethyl-4-(pyrrolidin-1-yl-carbonyl)-aniline, O-(benzotriazol-1-yl)-N,N,N',N'-tetramethyluroniumtetrafluoroborate and N-methylmorpholine in tetrahydrofuran.

Yield: 44% of theory, $R_f$ value: 0.75 (silica gel; ethyl acetate/ethanol=9:1)

g. 2-(5-carbamimidoyl-2-benzyloxy-phenyl)-N-[2,5-dimethyl-4-(pyrrolidin-1-yl-carbonyl)-phenyl]-acetamide Prepared analogously to Example 1e from 2-(5-cyano-2-benzyloxy-phenyl)-N-[2,5-dimethyl-4-(pyrrolidin-1-yl-carbonyl)-phenyl]-acetamide and hydrochloric acid/ammonium carbonate in ethanol.

Yield: 86% of theory, $R_f$ value: 0.20 (silica gel; methylene chloride/ethanol/glacial acetic acid=8:2:0.01)

h. 2-(5-carbamimidoyl-2-hydroxy-phenyl)-N-[2,5-dimethyl-4-(pyrrolidin-1-yl-carbonyl)-phenyl]-acetamide-hydrochloride 355 mg (0.68 mmol) of 2-(5-carbamimidoyl-2-benzyloxy-phenyl)-N-[2,5-dimethyl-4-(pyrrolidin-1-yl-carbonyl)-phenyl]-acetamide are dissolved in 40 ml of methanol and after the addition of 250 mg of palladium on active charcoal the mixture is hydrogenated with hydrogen for 15 minutes. Then the catalyst is filtered off and the filtrate is evaporated down.

Yield: 145 mg (49% of theory), $R_f$ value: 0.10 (silica gel; methylene chloride/ethanol/glacial acetic acid=8:2:0.01) $C_{22}H_{26}N_4O_3 \times HCl$ (394.48/430.94) mass spectrum: $(M+H)^+=395$ $(M-H)^-=393$ The following compounds are prepared analogously to Example 5:

(1) 2-(5-carbamimidoyl-2-hydroxy-phenyl)-N-[3-methyl-4-(piperidin-1-yl-carbonyl)-phenyl]-acetamide-hydrochloride Yield: 98% of theory, $R_f$ value: 0.75 (Reversed phase RP8; 5% saline solution/methanol=1:4) $C_{22}H_{26}N_4O_3 \times HCl$ (394.49/430.94) mass spectrum: $M^+=395$ $(M+Cl)^-=429/431$ (Cl) $(M-H)^-=393$ (2) 2-(5-carbamimidoyl-2-hydroxy-phenyl)-N-[3-methyl-4-(2-methyl-pyrrolidin-1-yl-carbonyl)-phenyl]-acetamide-hydrochloride Yield: 100% of theory, $R_f$ value: 0.7 (Reversed phase RP8; 5% saline solution/methanol=1:4) $C_{22}H_{26}N_4O_3 \times HCl$ (394.49/430.94) mass spectrum: $M^+=395$ $(M+Cl)^-=429/431$ (Cl) $(M-H)^-=393$

EXAMPLE 6

2-(2-benzyloxy-5-carbamimidoyl-phenyl)-N-(2-ethoxycarbonyl-ethyl)-N-[3-methyl-4-(pyrrolidin-1-yl-carbonyl)-phenyl]-acetamide-hydrochloride a. N-(2-methoxycarbonyl-ethyl)-3-methyl-4-(pyrrolidin-1-yl-carbonyl)-aniline 1.5 g (7.3 mmol) of 3-methyl-4-(pyrrolidin-1-yl-carbonyl)-aniline, 20 ml of (220 mmol) of methyl acrylate, 1 ml (2.2 mmol) of Triton B and 60 mg (0.27 mmol) of 2,5-di-tert.butyl-hydroquinone are stirred for 22 hours at 85° C. Then the reaction mixture is evaporated down, the residue is chromatographed on silica gel, eluting with methylene chloride+0 to 5% ethanol.

Yield: 1.6 g (76% of theory), $R_f$ value: 0.70 (silica gel; methylene chloride/ethanol=9:1)

b. 2-(2-benzyloxy-5-cyano-phenyl)-N-(2-ethoxycarbonyl-ethyl)-N-[3-methyl-4-(pyrrolidin-1-yl-carbonyl)-phenyl]-acetamide 0.8 g (2.88 mmol) of N-(2-methoxycarbonyl-ethyl)-3-methyl-4-(pyrrolidin-1-yl-carbonyl)-aniline are dissolved in 50 ml of tetrahydrofuran and after the addition of 1.1 ml (7.86 mmol) of triethylamine and 0.8 g (2.62 mmol) of 2-benzyloxy-5-cyano-phenylacetic acid chloride stirred for 8 hours at ambient temperature. Then the mixture is diluted with water and extracted with methylene chloride. The combined organic extracts are dried and evaporated down. The residue is chromatographed on silica gel, eluting with methylene chloride.

Yield: 1.0 g (71% of theory), $R_f$ value: 0.72 (silica gel; methylene chloride/ethanol=9:1)

c. 2-(2-benzyloxy-5-carbamimidoyl-phenyl)-N-(2-ethoxycarbonyl-ethyl)-N-[3-methyl-4-(pyrrolidin-1-yl-carbonyl)-phenyl]-acetamide-hydrochloride Prepared analogously to Example 1e from 2-(2-benzyloxy-5-cyano-phenyl)-N-(2-ethoxycarbonyl-ethyl)-N-[3-methyl-4-(pyrrolidin-1-yl-carbonyl)-phenyl]-acetamide and hydrochloric acid/ammonium carbonate in ethanol.

Yield: 44% of theory, $R_f$ value: 0.17 (silica gel; methylene chloride/ethanol=4:1) $C_{33}H_{38}N_4O_5 \times HCl$ (570.69/607.16) mass spectrum: (M+H)$^+$=571

EXAMPLE 7

2-(2-hydroxy-5-carbamimidoyl-phenyl)-N-(2-ethoxycarbonyl-ethyl)-N-[3-methyl-4-(pyrrolidin-1-yl-carbonyl)-phenyl]-acetamide-hydrochloride Prepared analogously to Example 5h from 2-(2-benzyloxy-5-carbamimidoyl-phenyl)-N-(2-ethoxycarbonyl-ethyl)-N-[3-methyl-4-(pyrrolidin-1-yl-carbonyl)-phenyl]-acetamide-hydrochloride and palladium on active charcoal in methanol.

Yield: 96% of theory, $R_f$ value: 0.45 (Reversed phase RP 8; methanol/5% sodium chloride solution=6:4) $C_{26}H_{32}N_4O_5 \times HCl$ (480.57/517.04) mass spectrum: (M+H)$^+$=481

EXAMPLE 8

2-(2-hydroxy-5-carbamimidoyl-phenyl)-N-(2-carboxy-ethyl)-N-[3-methyl-4-(pyrrolidin-1-yl-carbonyl)-phenyl]-acetamide-hydrochloride 0.3 g (0.58 mmol) of 2-(2-hydroxy-5-carbamimidoyl-phenyl)-N-(2-ethoxycarbonyl-ethyl)-N-[3-methyl-4-(pyrrolidin-1-yl-carbonyl)-phenyl]-acetamide-hydrochloride are stirred into a mixture of 3.2 ml (3.2 mmol) of 1-molar lithium hydroxide solution, 6.2 ml of water and 7.6 ml of tetrahydrofuran for 2 hours at ambient temperature. After the addition of 74 mg ammonium chloride the solution is evaporated down. The residue is chromatographed on the reversed phase and eluted with water.

Yield: 0.2 g (71% of theory), $R_f$ value: 0.62 (Reversed phase RP 8; methanol/5% sodium chloride solution=6:4) $C_{24}H_{28}N_4O_5 \times HCl$ (452.52/488.97) mass spectrum: (M+H)$^+$= 453 (M–H)$^-$=451

The following compounds are prepared analogously to Example 8:

(1) 2-(5-carbamimidoyl-2-hydroxy-phenyl)-N-[3-methyl-4-(N-(3-carboxypropionyl)-N-cyclopentyl-amino)-phenyl]-acetamide-hydrochloride Yield: 83% of theory, $C_{25}H_{30}N_4O_5 \times HCl$ (466.55/503.01) $R_f$ value: 0.84 (Reversed phase RP8; 5% saline solution/methanol=6:4)

(2) 2-(5-carbamimidoyl-2-hydroxy-phenyl)-N-[3-methyl-4-(N-carboxyacetyl-N-cyclopentyl-amino)-phenyl]-acetamide-hydrochloride

EXAMPLE 9

3-carbamimidoyl-N-[4-(pyrrolidin-3-yl-oxy)-benzyl]-benzamide-dihydrochloride a. N-tert.butyloxycarbonyl-3-pyrrolidinol 5.8 g (66.5 mmol) of 3-pyrrolidinol and 6.7 g (67 mmol) of triethylamine are dissolved in 80 ml of methylene chloride and a solution of 15.3 g (70 mmol) of di-tert.butyl-dicarbonate in 40 ml of methylene chloride is added dropwise. After 16 hours at ambient temperature the mixture is stirred with water, the organic phase is dried and evaporated down.

Yield: 12.4 g (100% of theory), $R_f$ value: 0.75 (silica gel; ethyl acetate/methanol=9:1)

b. 4-[(N-tert.butyloxycarbonyl)-pyrrolidin-3-yl-oxy]-benzonitrile 3.8 g (20 mmol) of N-tert.butyloxycarbonyl-3-pyrrolidinol are dissolved in 100 ml of tetrahydrofuran and after the addition of 2.4 g (20 mmol) of 4-hydroxybenzonitrile, 5.7 g (22 mmol) of triphenylphosphine and 3.9 g (22 mmol) of diethyl diethylazodicarboxylate the mixture is stirred for 18 hours at ambient temperature. The solvent is distilled off and the residue is chromatographed on silica gel, eluting with cyclohexane/ethyl acetate (10:5).

Yield: 4.5 g (78% of theory), $R_f$ value: 0.40 (silica gel; cyclohexane/ethyl acetate=10:5)

c. 4-[(N-tert.butyloxycarbonyl)-pyrrolidin-3-yl-oxy]-benzylamine 4.5 g (15.6 mmol) of 4-[(N-tert.butyloxycarbonyl)-pyrrolidin-3-yl-oxy]-benzonitrile are dissolved in 100 ml of methanol and 50 ml of methanolic ammonia and after the addition of 1 g of Raney nickel hydrogenated for 2 hours at 50° C. with hydrogen. Then the catalyst is filtered off and the filtrate is evaporated down.

Yield: 4.2 g (92% of theory), $R_f$ value: 0.08 (silica gel; ethyl acetate/methanol=4:1)

d. 3-cyano-N-[4-(N'-tert.butyloxycarbonyl-pyrrolidin-3-yl-oxy)-benzyl]-benzamide 1.1 g (3.8 mmol) of 4-[(N-tert.butyloxycarbonyl)-pyrrolidin-3-yl-oxy]-benzylamine are dissolved in 30 ml of methylene chloride and after the addition of 0.9 g (9 mmol) of triethylamine, 1.6 g (3.8 mmol) of 3-cyanobenzoic acid chloride are added batchwise. After 4 hours at ambient temperature the solution is combined with water, the organic phase is dried and evaporated down.

Yield: 1.5 g (94% of theory), $R_f$ value: 0.27 (silica gel; methylene chloride/ethyl acetate=9:1)

e. 3-carbamimidoyl-N-[4-(pyrrolidin-3-yl-oxy)-benzyl]-benzamide-dihydrochloride

Prepared analogously to Example 1e from 3-cyano-N-[4-(N'-tert.butyloxycarbonyl-pyrrolidin-3-yl-oxy)-benzyl]-benzamide and hydrochloric acid/ammonium chloride in ethanol.

Yield: 100% of theory, Melting point: from 180° C. (decomposition) $C_{19}H_{22}N_4O_2 \times 2$ HCl (338.41/411.41) mass spectrum: $(M+H)^+=339$ The following compounds are prepared analogously to Example 9:

(1) 3-carbamimidoyl-N-[4-(cyclopentyloxy)-benzyl]-benzamide-hydrochloride

Yield: 86% of theory $R_f$ value: 0.42 (silica gel; methylene chloride/ethanol=8:2) $C_{20}H_{23}N_3O_2 \times HCl$ (337.43/373.89) mass spectrum: $(M+H)^+=338$ (2) 3-carbamimidoyl-N-[4-(benzyloxy)-benzyl]-benzamide-hydrochloride Yield: 63% of theory $R_f$ value: 0.28 (silica gel: methylene chloride/ethanol=17:1) $C_{22}H_{21}N_3O_2 \times HCl$ (359.43/395.89) mass spectrum: $(M+H)^+=360$ (3) 3-carbamimidoyl-N-[4-(N'-acetyl-pyrrolidin-3-yl-oxy)-benzyl]-benzamide-hydrochloride Yield: 100% of theory, $R_f$ value: 0.08 (silica gel; methylene chloride/ethanol=9:1) $C_{21}H_{24}N_4O_3 \times HCl$ (380.45/416.91) mass spectrum: $(M+H)^+=381$ (4) 3-carbamimidoyl-N-[4-(N'-methyl-pyrrolidin-3-yl-oxy)-benzyl]-benzamide-hydrochloride Yield: 29% of theory, $R_f$ value: 0.07 (silica gel; methylene chloride/ethanol=7:3) $C_{20}H_{24}N_4O_2 \times HCl$ (352.44/388.91) mass spectrum: $(M+H)^+=353$ (5) 3-carbamimidoyl-N-[4-(N'-(aminomethylcarbonyl)-pyrrolidin-3-yl-oxy)-benzyl]-benzamide-dihydrochloride Yield: 82% of theory, Melting point: from 160° C. (decomposition) $C_{21}H_{25}N_5O_3 \times 2$ HCl (395.54/468.46) mass spectrum: $(M+H)^+=396$ (6) 3-carbamimidoyl-N-[4-(N'-(2-aminoethyl-carbonyl)-pyrrolidin-3-yl-oxy)-benzyl]-benzamide-dihydrochloride Yield: 88% of theory, Melting point: from 165° C. (decomposition) $C_{22}H_{27}N_5O_3 \times 2$ HCl (409.48/482.48) mass spectrum: $(M+H)^+=410$ (7) 3-carbamimidoyl-N-[4-(3-amino-propyloxy)-benzyl]-benzamide-dihydrochloride Yield: 82% of theory, Melting point: from 122° C. (decomposition) $C_{18}H_{22}N_4O_2 \times 2$ HCl (326.40/399.4) mass spectrum: $(M+H)^+=327$ (8) 3-carbamimidoyl-N-[4-(2-dimethylamino-ethyloxy)-benzyl]-benzamide-dihydrochloride Yield: 85% of theory, Melting point: from 65° C. (decomposition) $C_{19}H_{24}N_4O_2 \times 2$ HCl (340.43/413.43) mass spectrum: $(M+H)^+=341$ (9) 3-carbamimidoyl-N-[4-(pyridin-4-yl-oxy)-benzyl]-benzamide-hydrochloride Yield: 66% of theory, Melting point: 115° C. (decomposition) $C_{20}H_{18}N_4O_2 \times HCl$ (346.39/382.89) mass spectrum: $(M+H)^+=347$

(10) 3-carbamimidoyl-N-[4-(piperidin-4-yl-oxy)-benzyl]-benzamide-hydrochloride

Yield: 62% of theory Melting point: from 170° C. (decomposition) $C_{20}H_{24}N_4O_2 \times HCl$ (352.44/388.89) mass spectrum: $(M+H)^+=353$

EXAMPLE 10

3-carbamimidoyl-N-[4-(1-(1-imino-ethyl)-pyrrolidin-3-yl-oxy)-benzyl]-benzamide-dihydrochloride a. 3-cyano-N-[4-(pyrrolidin-3-yl-oxy)-benzyl]-benzamide 2.4 g (5.7 mmol) of 3-cyano-N-[4-(N-tert.butyloxycarbonyl-pyrrolidin-3-yl-oxy)-benzyl]-benzamide are dissolved in 30 ml of methylene chloride and at 0C combined with 8 ml of trifluoroacetic acid. After 1 hour at ambient temperature the solvent is distilled off, the residue is taken up in methylene chloride, made alkaline with ammonia and water is added. The combined organic extracts are dried and evaporated down.

Yield: 1.4 g (76% of theory), $R_f$ value: 0.29 (silica gel; methylene chloride/methanol/ammonia=7:3:0.2)

b. 3-cyano-N-[4-(1-(1-imino-ethyl)-pyrrolidin-3-yl-oxy)-benzyl]-benzamide 0.7 g (2.17 mmol) of 3-cyano-N-[4-(pyrrolidin-3-yl-oxy)-benzyl]-benzamide, 0.4 g (3.2 mmol) of ethyl acetimidate hydrochloride and 1 g (10 mmol) of triethylamine are dissolved in 70 ml of ethanol and the mixture is stirred for 6 days at ambient temperature. The solvent is distilled off, the residue is taken up in water and made alkaline with sodium carbonate. Then it is extracted with methylene chloride, the combined organic extracts are dried and evaporated down. The residue is triturated with ether and suction filtered.

Yield: 0.6 g (76% of theory), $R_f$ value: 0.37 (silica gel; methylene chloride/methanol/ammonia=7:3:0.2) Melting point: from 80° C. (decomposition)

c. 3-carbamimidoyl-N-[4-(1-(1-imino-ethyl)-pyrrolidin-3-yl-oxy)-benzyl]-benzamide-dihydrochloride Prepared analogously to Example 1e from 3-cyano-N-[4-(1-(1-imino-ethyl)-pyrrolidin-3-yl-oxy)-benzyl]-benzamide and hydrochloric acid/ammonium carbonate in ethanol.

Yield: 64% of theory, Melting point: from 100° C. (decomposition) $C_{21}H_{25}N_5O_2 \times 2$ HCl (379.46/452.46) mass spectrum: $(M+H)^+=380$ The following compound is prepared analogously to Example 10:

(1) 3-carbamimidoyl-N-[4-(1-carbamimidoyl-pyrrolidin-3-yl-oxy)-benzyl]-benzamide-dihydrochloride Yield: 88% of theory, Melting point: from 160° C. (decomposition) $C_{20}H_{24}N_6O_2 \times 2$ HCl (380.45/453.38) mass spectrum: $(M+2H)^{++}=191$

EXAMPLE 11

3-carbamimidoyl-N-[4-(benzoylamino)-benzyl]-benzamide-hydrochloride a. 3-cyano-N-(4-amino-benzyl)-benzamide 6 g (0.05 mol) of 4-aminobenzylamine and 10 g (0.1 mol) of triethylamine are dissolved in 150 ml of methylene chlo ride and at ambient temperature a solution of 8.3 g (0.05 mol) of 3-cyanobenzoylchloride in 20 ml of methylene chloride is added dropwise. After one hour 150 ml of water and 20 ml of methanol are added. After extraction the combined organic extracts are dried and evaporated down. The residue is chromatographed on silica gel and eluted with ethyl acetate.

Yield: 4.4 g (35% of theory), $R_f$ value: 0.69 (silica gel; ethyl acetate)

b. 3-cyano-N-[4-(benzoylamino)-benzyl]-benzamide

A solution of 0.6 g (4.2 mmol) of benzoylchloride in 10 ml of methylene chloride is added dropwise to a solution of 1 g (4 mmol) of 3-cyano-N-(4-amino-benzyl)-benzamide and 0.6 g (6 mmol) of triethylamine in 30 ml of methylene chloride at ambient temperature. After 8 hours at ambient temperature the product which has crystallised out is dissolved in methylene chloride and methanol. After extraction with water the combined organic extracts are dried and evaporated down.

Yield: 1.2 g (84% of theory), Melting point: 210° C.

c. 3-carbamimidoyl-N-[4-(benzoylamino)-benzyl]-benzamide-hydrochloride

Prepared analogously to Example 1e from 3-cyano-N-[4-(benzoylamino)-benzyl]-benzamide and hydrochloric acid/ammonium carbonate in ethanol.

Yield: 65% of theory, Melting point: 190-215° C. $C_{22}H_{20}N_4O_2 \times HCl$ (372.43/408.93) mass spectrum: $(M+H)^+= 373$ The following compounds are prepared analogously to Example 11:

(1) 3-carbamimidoyl-N-[4-(phenylsulphonylamino)-benzyl]-benzamide-hydrochloride

Yield: 80% of theory, Melting point: 266° C. $C_{21}H_{20}N_4O_3S \times HCl$ (408.48/444.98) mass spectrum: $(M+H)^+=409$ (2) 3-carbamimidoyl-N-[4-(benzylamino)-benzyl]-benzamide-hydrochloride Yield: 69% of theory, $C_{22}H_{22}N_4O \times HCl$ (358.44/394.94) mass spectrum: $(M+H)^+=359$ (3) 3-carbamimidoyl-N-[4-(N-benzyl-N-ethoxycarbonyl-methyl-amino)-benzyl]-benzamide-hydrochloride Yield: 79% of theory, Melting point: from 100° C. $C_{26}H_{28}N_4O_3 \times HCl$ (444.54/481.04) mass spectrum: $(M+H)^+= 445$ (4) 3-carbamimidoyl-N-[4-biphenyl-methyl]-benzamide Yield: 79% of theory, Melting point: from 160° C. (decomposition) $C_{21}H_{19}N_3O$ (329.40) mass spectrum: $(M+H)^+=330$ (5) 3-carbamimidoyl-N-[4-(cyclopentylamino)-benzyl]-benzamide-hydrochloride Yield: 80% of theory, Melting point: from 135° C. (decomposition) $C_{20}H_{24}N_4O \times HCl$ (336.44/372.94) mass spectrum: $M^+=336$

EXAMPLE 12

3-carbamimidoyl-N-(4-dimethylaminomethyl-benzyl)-benzamide-dihydrochloride a. 4-cyano-N.N-dimethyl-benzylamine A solution of 7.3 g (0.16 mol) of dimethylamine in 100 ml of ether is added dropwise at −5° C. to a solution of 10 g (0.05 mol) of 4-cyanobenzylbromide in 400 ml of ether. Then the reaction mixture is stirred for 2 hours at −5° C. and for 20 hours at ambient temperature. After the addition of 200 ml of water and 200 ml of conc. hydrochloric acid the aqueous solution is separated off, made alkaline with sodium hydroxide solution and extracted with methylene chloride. The combined organic extracts are dried and evaporated down.

Yield: 8 g (100% of theory), $R_f$ value: 0.58 (silica gel; methylene chloride/ethanol=9: 1)

b. 4-dimethylaminomethyl-benzylamine

Prepared analogously to Example 9c from 4-cyano-N.N-dimethyl-benzylamine, methanolic ammonia and Raney nickel/hydrogen.

Yield: 94% of theory, $R_f$ value: 0.13 (silica gel; methylene chloride/ethanol=9:1)

c. 3-cyano-N-(4-dimethylaminomethyl-benzyl)-benzamide

Prepared analogously to Example 9d from 4-dimethylaminomethyl-benzylamine, 3-cyanobenzoylchloride and triethylamine in methylene chloride.

Yield: 73% of theory, Melting point: 100° C.

d. 3-carbamimidoyl-N-(4-dimethylaminomethyl-benzyl)-benzamide-dihydrochloride

Prepared analogously to Example 1e from 3-cyano-N-(4-dimethylaminomethyl-benzyl)-benzamide and hydrochloric acid/ammonium carbonate in ethanol.

Yield: 100% of theory, Melting point: from 101° C. (decomposition) $C_{18}H_{22}N_4O \times 2$ HCl (310.40/383.40) mass spectrum: $(M+H)^+=311$ The following compounds are prepared analogously to Example 12:

(1) 3-carbamimidoyl-N-[4-(imidazol-1-yl)-methyl-benzyl]-benzamide-hydrochloride

Yield: 86% of theory, Melting point: from 152° C. (decomposition) $C_{19}H_{19}N_5O \times HCl$ (333.39/369.89) mass spectrum: $(M+H)^+=334$ (2) 2-(5-carbamimidoyl-2-hydroxy-phenyl)-N-[3-methyl-4-(pyrrolidin-1-yl-methyl)-phenyl]-acetamide-dihydrochloride Yield: 60% of theory $R_f$ value (reversed phase RP8; 5% saline solutio/methanol=2:3): 0.7 $C_{21}H_{26}N_4O_2 \times 2$ HCl (366.47/439.38) mass spectrum: $(M+H)^+=367$ $(M-H)^-=365$ (3) 2-(5-carbamimidoyl-2-hydroxy-phenyl)-N-[3-methyl-4-(imidazol-1-yl-methyl)-phenyl]-acetamide-dihydrochloride Yield: 57% of theory $R_f$ value (reversed phase RP8; 5% saline solution/methanol=2:3): 0.7 $C_{20}H_{21}N_5O_2 \times 2$ HCl (363.42/436.33) mass spectrum: $(M+H)^+=364$ $(M-H)^-=362$ (4) 2-(5-carbamimidoyl-2-hydroxy-phenyl)-N-[3-methyl-4-(2-methyl-imidazol-1-yl-methyl)-phenyl]-acetamide-dihydrochloride

EXAMPLE 13

2-(5-carbamimidoyl-2-hydroxy-phenyl)-N-[3-methyl-4-(2-aminosulphonyl-phenyl)-phenyl]-acetamide-hydrochloride a. 3-Allyl-4-hydroxy-benzonitrile 82.3 g (0.52 mol) of 4-allyloxy-benzonitrile are heated to 200° C. for 2 hours under a nitrogen atmosphere. After cooling, the crude product is purified on silica gel, eluting first with petroleum ether, later with petroleum ether/ethyl acetate (9:1, 8:2, 7:3 and 1:1). The uniform fractions are combined and evaporated down, the residue is washed with petroleum ether and dried.

Yield: 43 g (52% of theory), $R_f$ value: 0.45 (silica gel; petroleum ether/ethyl acetate=1:1) $C_{10}H_9NO$ (159.19) mass spectrum: $(M-H)^-=158$ $(2M+Na)^+=341$ b. 3-Allyl-4-benzyloxy-benzonitrile Prepared analogously to Example 5d from 3-allyl-4-hydroxy-benzonitrile and benzylbromide/potassium carbonate in dimethylformamide.

Yield: 90% of theory, Melting point: 59-60° C. $R_f$ value: 0.55 (silica gel; petroleum ether/ethyl acetate=4:1)

c. 2-benzyloxy-5-cyano-phenylacetic acid 30 g (0.12 mol) of 3-allyl-4-benzyloxy-benzonitrile are dissolved in 450 ml of acetonitrile and at 40° C. 0.7 g of ruthenium trichloride hydrate and a solution of 179.7 g (0.84 mol) of sodium periodate in 1 litre of water is added. After it has all been added, the reaction mixture is heated to 40° C. for a further 30 minutes and then extracted 3× with 1 litre of ethyl acetate. The organic phases are washed with saline solution and dried over sodium sulphate. The crude product is recrystallised from petroleum ether/ethyl acetate (7:3) with the addition of activated charcoal.

Yield: 18.4 g (58% of theory), Melting point: 144-145° C. $R_f$ value: 0.2 (silica gel; petroleum ether/ethyl acetate=1:1) $C_{16}H_{13}NO_3$ (267.29) mass spectrum: $(M-H)^-=266$ $(M+Na)^+=290$ d. 2-(5-cyano-2-benzyloxy-phenyl)-N-[3-methyl-4-(2-tert.butylaminosulphonyl-phenyl)-phenyl]-acetamide Prepared analogously to Example 1b from 2-benzyloxy-5-cyano-phenylacetic acid and 4'-amino-2'-methyl-biphenyl-2-sulphonic acid-tert.-butylamide/O-(benzotriazol-1-yl)-N,N,N',N'-tetramethyluronium tetrafluoroborate/triethylamine in dimethylformamide.

Yield: 60% of theory, $R_f$ value: 0.5 (silica gel; methylene chloride/ethanol=19:1)

e. 2-(5-carbamimidoyl-2-benzyloxy-phenyl)-N-[3-methyl-4-(2-aminosulphonyl-phenyl)-phenyl]-acetamide-hydrochloride Prepared analogously to Example 1e from 2-(5-cyano-2-benzyloxy-phenyl)-N-[3-methyl-4-(2-tert.butylaminosulphonyl-phenyl)-phenyl]-acetamide and hydrochloric acid/ammonium carbonate in ethanol.

Yield: 70% of theory, $R_f$ value: 0.3 (silica gel; methylene chloride/ethanol=9:1+1% glacial acetic acid) $C_{29}H_{28}N_4O_4S\times HCl$ (528.63/565.08) mass spectrum: $(M-H)^-=527$ $(M+H)^+=529$ f. 2-(5-carbamimidoyl-2-hydroxy-phenyl)-N-[3-methyl-4-(2-aminosulphonyl-phenyl)-phenyl]-acetamide-hydrochloride Prepared analogously to Example 5h from 2-(5-carbamimidoyl-2-benzyloxy-phenyl)-N-[3-methyl-4-(2-aminosulphonyl-phenyl)-phenyl]-acetamide-hydrochloride and hydrogen/palladium on activated charcoal.

Yield: 62% of theory, $R_f$ value: 0.45 (Reversed phase RP8; 5% saline solution/methanol=1:1) $C_{22}H_{22}N_4O_4S\times HCl$ (438.52/474.97) mass spectrum: $(M+H)^+=439$ $(M+Cl)^-=473/5$ (Cl)

The following compounds are prepared analogously to Example 13:

(1) 2-(5-carbamimidoyl-2-hydroxy-phenyl)-N-(3-methyl-4-phenyl-phenyl)-acetamide-hydrochloride Yield: 13% of theory, $R_f$ value: 0.15 (silica gel; methylene chloride/ethanol=4:1) $C_{22}H_{21}N_3O_2\times HCl$ (359.45/395.9) mass spectrum: $(M+H)^+=360$ $(M-H)^-=358$ (2) 2-(5-carbamimidoyl-2-hydroxy-phenyl)-N-[3-methyl-4-(2-aminosulphonyl-5-methyl-phenyl)-phenyl]-acetamide-hydrochloride Yield: 23% of theory $R_f$ value (silica; methylene chloride/ethanol=7:3): 0.3 $C_{23}H_{24}N_4O_4S\times HCl$ (452.54/488.99) mass spectrum: $(M+H)^+=453$ $(M-H)^-=451$

EXAMPLE 14

2-[5-(N-benzoyl-carbamimidoyl)-2-hydroxy-phenyl]-N-[3-methyl-4-(pyrrolidin-1-yl-carbonyl)-phenyl]-acetamide a. 2-[5-(N-benzoyl-carbamimidoyl)-2-benzyloxy-phenyl]-N-[3-methyl-4-(pyrrolidin-1-yl-carbonyl)-phenyl]-acetamide 350 mg (0.69 mmol) of 2-(5-carbamimidoyl-2-benzyloxy-phenyl)-N-[3-methyl-4-(pyrrolidin-1-yl-carbonyl)-phenyl]-acetamide-hydrochloride are suspended in 40 ml of methylene chloride and combined with 1.0 ml of triethylamine and 300 mg (1.3 mmol) of 4-nitrophenylbenzoate. The reaction mixture is refluxed for 4 hours. After the addition of 100 ml of saline solution the aqueous phase is extracted 3× with methylene chloride. The combined organic phases are dried over sodium sulphate and concentrated by evaporation.

The crude product is purified on silica gel, eluting first with methylene chloride, then with methylene chloride/ethanol (50:1 and 19:1). The uniform fractions are combined, concentrated by evaporation and stirred with petroleum ether/ether (1:1). The solid formed is suction filtered and dried.

Yield: 280 mg (71% of theory), $R_f$ value: 0.2 (silica gel; petroleum ether/ethyl acetate=1:1) $C_{35}H_{34}N_4O_4$ (574.69) mass spectrum: $(M-H)^-=573$ $(M+H)^+=575$ b. 2-[5-(N-benzoyl-carbamimidoyl)-2-hydroxy-phenyl]-N-[3-methyl-4-(pyrrolidin-1-yl-carbonyl)-phenyl]-acetamide Prepared analogously to Example 5h from 2-[5-(N-benzoyl-carbamimidoyl)-2-benzyloxy-phenyl]-N-[3-methyl-4-(pyrrolidin-1-yl-carbonyl)-phenyl]-acetamide and hydrogen/palladium on activated charcoal.

Yield: 31% of theory, $R_f$ value: 0.3 (silica gel; methylene chloride/ethanol=19:1) $C_{28}H_{28}N_4O_4$ (484.56) mass spectrum: $(M+H)^+=485$ $(M+Na)^+=507$ The following compounds are prepared analogously to Example 14:

(1) 2-[5-(N-n-hexyloxycarbonyl-carbamimidoyl)-2-hydroxy-phenyl]-N-[3-methyl-4-(pyrrolidin-1-yl-carbonyl)-phenyl]-acetamide Yield: 17% of theory, $R_f$ value: 0.3 (silica gel; methylene chloride/ethanol=4:1) $C_{28}H_{36}N_4O_5$ (508.62) mass spectrum: $(M+H)^+=509$ $(M-H)^-=507$ (2) 2-[5-(N-benzoyl-carbamimidoyl)-2-methoxy-phenyl]-N-[3-methyl-4-(pyrrolidin-1-yl-carbonyl)-phenyl]-acetamide Yield: 40% of theory, $R_f$ value: 0.3 (silica gel; methylene chloride/ethanol=19:1) $C_{29}H_{30}N_4O_4$ (498.59) mass spectrum: $(M+H)^+=499$ $(M-H)^-=497$ (3) 2-[5-(N-n-hexyloxycarbonyl-carbamimidoyl)-2-methoxy-phenyl]-N-[3-methyl-4-(pyrrolidin-1-yl-carbonyl)-phenyl]-acetamide Yield: 35% of theory, $R_f$ value: 0.25 (silica gel; methylene chloride/ethanol=19:1) $C_{29}H_{28}N_4O_5$ (522.65) mass spectrum: $(M+H)^+=523$ $(M-H)^-=521$ $(M+Na)^+=545$ (4) 2-[5-(N-ethyloxycarbonyl-carbamimidoyl)-2-methoxy-phenyl]-N-[3-methyl-4-(pyrrolidin-1-yl-carbonyl)-phenyl]-acetamide Yield: 32% of theory, $R_f$ value: 0.45 (silica gel; methylene chloride/ethanol=9:1) $C_{25}H_{30}N_4O_5$ (466.54) mass spectrum: $(M+H)^+=467$ $(M-H)^-=465$ $(M+Na)^+=489$

EXAMPLE 15

2-[5-(N-hydroxy-carbamimidoyl)-2-hydroxy-phenyl]-N-[3-methyl-4-(pyrrolidin-1-yl-carbonyl)-phenyl]-acetamide-acetate a. 2-[5-(N-hydroxy-carbamimidoyl)-2-benzyloxy-phenyl]-N-[3-methyl-4-(pyrrolidin-1-yl-carbonyl)-phenyl]-acetamide-acetate 1.1 g (2.5 mmol) of 2-(5-cyano-2-benzyloxy-phenyl)-N-[3-methyl-4-(pyrrolidin-1-yl-carbonyl)-phenyl]-acetamide are dissolved in 100 ml of methanol and combined with a solution of 300 mg (5 mmol) of hydroxylamine hydrochloride in 2.0 ml of water. After the addition of 800 mg (2.5 mmol) of caesium carbonate and 300 mg (3.0 mmol) of sodium carbonate the reaction mixture is refluxed for 6 hours. After cooling and the addition of 0.5 l of ice water the crude product obtained is suction filtered and purified on silica gel, eluting first with methylene chloride and methylene chloride/ethanol (19:1), then with methylene chloride/ethanol (9:1+1% glacial acetic acid and 4:1+1% glacial acetic acid). The uniform fractions are combined and concentrated by evaporation.

Yield: 620 mg (51% of theory), $R_f$ value: 0.3 (silica gel; methylene chloride/ethanol=9:1) $C_{28}H_{30}N_4O_4$ (486.58) mass spectrum: $(M-H)^-=485$ $(M+H)^+=487$ $(M+Na)^+=509$ b. 2-[5-(N-hydroxy-carbamimidoyl)-2-hydroxy-phenyl]-N-[3-methyl-4-(pyrrolidin-1-yl-carbonyl)-phenyl]-acetamide-acetate Prepared analogously to Example 5h from 2-[5-(N-hydroxy-carbamimidoyl)-2-benzyloxy-phenyl]-N-[3-methyl-4-(pyrrolidin-1-yl-carbonyl)-phenyl]-acetamide-acetate and hydrogen/palladium on activated charcoal.

Yield: 50% of theory, 30 $R_f$ value: 0.25 (silica gel; methylene chloride/ethanol=4:1+1% glacial acetic acid) $C_{21}H_{24}N_4O_4 \times CH_3COOH$ (396.45/456.5) mass spectrum: $(M+H)^+=397$ $(M-H)^-=395$ The following compound is prepared analogously to Example 15:

(1) 2-[5-(N-hydroxy-carbamimidoyl)-2-methoxy-phenyl]-N-[3-methyl-4-(pyrrolidin-1-yl-carbonyl)-phenyl]-acetamide-acetate Yield: 7% of theory, $R_f$ value: 0.28 (silica gel; methylene chloride/ethanol=4:1+1% glacial acetic acid) $C_{22}H_{26}N_4O_4 \times CH3COOH$ (410.48/470.52) mass spectrum: $(M+H)^+=411$ $(M-H)^-=409$ $(M+Na)^+=433$

EXAMPLE 16

Dry ampoule containing 75 mg of active substance per 10 ml

Composition:

| | |
|---|---|
| Active substance | 75.0 mg |
| Mannitol | 50.0 mg |
| water for injections | ad 10.0 ml |

Preparation:

Active substance and mannitol are dissolved in water. After packaging the solution is freeze-dried. To produce the solution ready for use, the product is dissolved in water for injections.

EXAMPLE 17

Dry ampoule containing 35 mg of active substance per 2 ml

Composition:

| | |
|---|---|
| Active substance | 35.0 mg |
| Mannitol | 100.0 mg |
| water for injections | ad 2.0 ml |

Preparation:

Active substance and mannitol are dissolved in water. After packaging, the solution is freeze-dried.

To produce the solution ready for use, the product is dissolved in water for injections.

EXAMPLE 18

Tablet containing 50 mg of active substance

Composition:

| | |
|---|---|
| (1) Active substance | 50.0 mg |
| (2) Lactose | 98.0 mg |
| (3) Maize starch | 50.0 mg |
| (4) Polyvinylpyrrolidone | 15.0 mg |
| (5) Magnesium stearate | 2.0 mg |
| | 215.0 mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 9 mm.

EXAMPLE 19

Tablet containing 350 mg of active substance

Composition:

| | |
|---|---|
| (1) Active substance | 350.0 mg |
| (2) Lactose | 136.0 mg |
| (3) Maize starch | 80.0 mg |
| (4) Polyvinylpyrrolidone | 30.0 mg |
| (5) Magnesium stearate | 4.0 mg |
| | 600.0 mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 12 mm.

EXAMPLE 20

Capsules containing 50 mg of active substance

Composition:

| | |
|---|---|
| (1) Active substance | 50.0 mg |
| (2) Dried maize starch | 58.0 mg |
| (3) Powdered lactose | 50.0 mg |
| (4) Magnesium stearate | 2.0 mg |
| | 160.0 mg |

Preparation:

(1) is triturated with (3). This trituration is added to the mixture of (2) and (4) with vigorous mixing.

This powder mixture is packed into size 3 hard gelatine capsules in a capsule filling machine.

EXAMPLE 21

Capsules containing 350 mg of active substance

Composition:

| | |
|---|---|
| (1) Active substance | 350.0 mg |
| (2) Dried maize starch | 46.0 mg |
| (3) Powdered lactose | 30.0 mg |
| (4) Magnesium stearate | 4.0 mg |
| | 430.0 mg |

Preparation:

(1) is triturated with (3). This trituration is added to the mixture of (2) and (4) with vigorous mixing.

This powder mixture is packed into size 0 hard gelatine capsules in a capsule filling machine.

EXAMPLE 22

Suppositories containing 100 mg of active substance 1 suppository contains:

| | |
|---|---|
| Active substance | 100.0 mg |
| Polyethyleneglycol (M.W. 1500) | 600.0 mg |
| Polyethyleneglycol (M.W. 6000) | 460.0 mg |
| Polyethylenesorbitan monostearate | 840.0 mg |
| | 2,000.0 mg |

Preparation:

The polyethyleneglycol is melted together with polyethylenesorbitan monostearate. At 40° C. the ground active substance is homogeneously dispersed in the melt. This is then cooled to 38° C. and poured into slightly chilled suppository moulds.

The invention claimed is:

1. A carboxylic acid amide compound of the following formula

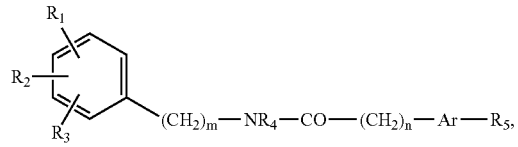

wherein m denotes the number 0 and n denotes the number 1,

Ar denotes a phenylene group substituted by a fluorine, chlorine or bromine atom, by a trifluoromethyl, $C_{1-3}$ alkyl, hydroxy, $C_{1-3}$ alkoxy, phenyl-$C_{1-3}$ alkoxy, amino, $C_{1-3}$ alkylamino or di ($C_{1-3}$ alkyl)-amino group, said phenylene group optionally substituted by a second fluorine, chlorine or bromine atom or by a second $C_{1-3}$ alkyl group or Ar denotes a naphtylene group optionally substituted by a fluorine, chlorine or bromine atom, by a trifluoromethyl, $C_{1-3}$ alkyl, hydroxy, $C_{1-3}$ alkoxy, phenyl-$C_{1-3}$ alkoxy, amino, $C_{1-3}$ alkylamino or di ($C_{1-3}$ alkyl)-amino group, said phenylene group optionally substituted by a second fluorine, chlorine or bromine atom or by a second $C_{1-3}$ alkyl group, R1 denotes a pyrrolidinocarbonyl or piperdinocarbonyl optionally substituted with a $C_{1-3}$ alkyl group, R2 denotes a hydrogen, fluorine, chlorine or bromine atom, a $C_{1-3}$ alkyl, hydroxy or $C_{1-3}$ alkoxy group, R3 denotes a hydrogen atom or a $C_{1-3}$ alkyl group, R4 denotes a hydrogen atom or a $C_{1-3}$ alkyl group optionally substituted by a carboxy group, and R5 denotes a cyano group or an amidino group, wherein said amidino group is optionally substituted by one or two $C_{1-3}$ alkyl groups or by a $C_{1-6}$ alkoxycarbony or benzoyl group or stereoisomer or salt thereof.

2. The compound of formula I according to claim 1 wherein m denotes the number 0 and n denotes the number 1, Ar denotes a phenylene group substituted by a fluorine, chlorine or bromine atom or by a methyl, hydroxy, methoxy or benzyloxy group, which may be substituted by another methyl group, R1 denotes a pyrrolidinocarbonyl or piperdinocarbonyl optionally substituted with a $C_{1-3}$ alkyl group, R2 denotes a hydrogen, fluorine, chlorine or bromine atom, a methyl, hydroxy or methoxy group, R3 denotes a hydrogen atom or a methyl group, R4 denotes a hydrogen atom or a methyl or ethyl group optionally substituted by a carboxy or $C_{1-3}$ alkoxycarbonyl group, and R5 denotes a cyano group or an amidino group wherein said amidino group is optionally substituted by a $C_{1-6}$ alkoxycarbonyl or benzoyl group;

or stereoisomer or salt thereof.

3. The compounds of formula I according to claim 1, wherein m denotes the number 0 and n denotes the number 1, Ar denotes a phenylene group substituted by a methyl, hydroxy, methoxy or benzyloxy group, R1 denotes a pyrrolidinocarbonyl or piperidinocarbonyl optionally substituted with a methyl group, R2 denotes a hydrogen, fluorine, chlorine or bromine atom or a methyl group, R3 denotes a hydrogen atom or a methyl group, R4 denotes a hydrogen atom or a methyl or ethyl group substituted by a carboxy, methoxycarbonyl or ethoxycarbonyl group, and R5 denotes an amidino group wherein said amidino group is optionally substituted by a $C_{1-6}$ alkoxycarbonyl or benzoyl group or stereoisomer or salt thereof.

4. A compound of the formula I according to claim 1 selected from the following compounds:
(a) 2-(5-carbamimidoyl-2-hydroxy-phenyl)-N-[3-methyl-4-(pyrrolidin-1-yl-carbonyl)-phenyl]-acetamide,
(b) 2-(2-benzyloxy-5-carbamimidoyl-phenyl)-N-(2-ethoxycarbonyl-ethyl)-N-[3-methyl-4-(pyrrolidin-1-yl-carbonyl)-phenyl]-acetamide,
(c) 2-(2-hydroxy-5-carbamimidoyl-phenyl)-N-(2-ethoxycarbonylethyl)-N-[3-methyl-4-(pyrrolidin-1-yl-carbonyl)-phenyl]-acetamide,
(d) 2-(2-hydroxy-5-carbamimidoyl-phenyl)-N-(2-carboxy-ethyl)-N[3methyl-4-(pyrrolidin-1-yl-carbonyl)-phenyl]-acetamide,
(e) 2-(5-carbamimidoyl-2-hydroxy-phenyl)-N-[3-methyl-4-(piperidin-1-yl-carbonyl)-phenyl]-acetamide and
(f) 2-(5-carbamimidoyl-2-hydroxy-phenyl)-N-[3-methyl-4(2 aminosulphonyl-phenyl)-phenyl]-acetamide,
wherein the amidino group may additionally be substituted by a $C_{1-6}$ alkoxycarbonyl or benzoyl group, or stereoisomer.

5. A compound of formula 1 according to claim 1 wherein the compound is 2-(5-Carbamimidoyl-2-hydroxy-phenyl)-N-[3-methyl-4-(pyrrolidin-1-yl-carbonyl)-phenyl]-acetamide or stereoisomer or a salt thereof.

6. A pharmaceutical composition comprising a compound according to claim 1 or a physiologically acceptable salt thereof together with one or more inert carriers, diluents, or both carriers and diluents.

7. A pharmaceutical composition containing a compound according to claim 3 or a physiologically acceptable salt thereof, optionally together with one or more inert carrier, diluents, or both carriers and diluents.

8. A compound of the formula I according to claim 1 selected from the following compounds:
(a) 2-(5-carbamimidoyl-2-hydroxy-phenyl)-N-[3-methyl-4-(pyrrolidin-1-yl-carbonyl)-phenyl]-acetamide,
(c) 2-(5-carbamimidoyl-2-hydroxy-phenyl)-N-methyl-N-[3-methyl-4-(pyrrolidin-1-yl-carbonyl)-phenyl]-acetamide,
(d) 2-(5-carbamimidoyl-2-benzyloxy-phenyl)-N-methyl-N-[3-methyl-4-(pyrrolidin-1-yl-carbonyl)-phenyl]-acetamide,
(e) 2-(5-carbamimidoyl-2-hydroxy-phenyl)-N-[3-methyl-4(N (3ethoxycarbonyl-propionyl)-N-cyclopentyl-amino)-phenyl]-acetamide,
(f) 2-(5-carbamimidoyl-2-hydroxy-phenyl)-N-[2,5-dimethyl-4-(pyrrolidin-1-yl-carbonyl)-phenyl]-acetamide,
(g) 2-(5-carbamimidoyl-2-hydroxy-phenyl)-N-[3-methyl-4-(piperidin-1-yl-carbonyl)-phenyl]-acetamide and
(h) 2-(5-carbamimidoyl-2-hydroxy-phenyl)-N-[3-methyl-4-(2-methyl-pyrrolidin-1-yl-carbonyl)-phenyl]-acetamide,
(i) 2-(2-benzyloxy-5-carbamimidoyl-phenyl)-N-(2-ethoxycarbonyl-ethyl)-N-[3-methyl-4-(pyrrolidin-1-yl-carbonyl)-phenyl]-acetamide,
(j) 2-(2-hydroxy-5-carbamimidoyl-phenyl)-N-(2-ethoxycarbonylethyl)-N-[3-methyl-4-(pyrrolidin-1-yl-carbonyl)-phenyl]-acetamide,
(k) 2-(2-hydroxy-5-carbamimidoyl-phenyl)-N-(2-carboxy-ethyl)-N[3 methyl-4-(pyrrolidin-1-yl-carbonyl)-phenyl]-acetamide,
(l) 2-[5-(N-benzoyl-carbamimidoyl)-2-hydroxy-phenyl]-N-[3-methyl-4(pyrrolidin-1-yl-carbonyl)-phenyl]-acetamide,
(m) 2-[5-(N-n-hexyloxycarbonyl-carbamimidoyl)-2-hydroxy-phenyl]-N-[3-methyl-4-(pyrrolidin-1-yl-carbonyl)-phenyl]-acetamide,
(n) 2-[5-(N-benzoyl-carbamimidoyl)-2-methoxy-phenyl]-N[3methyl-4-(pyrrolidin-1-yl-carbonyl)-phenyl]-acetamide,
(o) 2-[5-(N-n-hexyloxycarbonyl-carbamimidoyl)-2-methoxy-phenyl]-N-[3-methyl-4-(pyrrolidin-1-yl-carbonyl)-phenyl]-acetamide,
(p) 2-[5-(N-ethyloxycarbonyl-carbamimidoyl)-2-methoxy-phenyl]-N[3methyl-4-(pyrrolidin-1-yl-carbonyl)-phenyl]-acetamide, or stereoisomer or salt thereof.

9. A compound of the formula I according to claim 1 selected from the following compounds:
(q) 2-[5-(N-hydroxy-carbamimidoyl)-2-hydroxy-phenyl]-N-[3-methyl-4-(pyrrolidin-1-yl-carbonyl)-phenyl]-acetamide,
(r) 2-[5-(N-hydroxy-carbamimidoyl)-2-methoxy-phenyl]-N[3methyl-4-(pyrrolidin-1-yl-carbonyl)-phenyl]-acetamide, or stereoisomer or salt thereof.

* * * * *